(12) United States Patent
Okada et al.

(10) Patent No.: US 6,753,190 B1
(45) Date of Patent: Jun. 22, 2004

(54) IMMUNOLOGIC TEST METHOD AND IMMUNOLOGIC TEST KIT

(75) Inventors: Keisaku Okada, Ibaraki (JP); Takeshi Saika, Ibaraki (JP); Shuji Senda, Ibaraki (JP); Kenjiro Mori, Ibaraki (JP); Ken Sato, Ibaraki (JP)

(73) Assignee: Nitto Denko Corporation, Osaka (JP)

( * ) Notice: Subject to any disclaimer, the term of this patent is extended or adjusted under 35 U.S.C. 154(b) by 0 days.

(21) Appl. No.: 09/486,640

(22) PCT Filed: Jun. 30, 1999

(86) PCT No.: PCT/JP99/03539

§ 371 (c)(1),
(2), (4) Date: Feb. 29, 2000

(87) PCT Pub. No.: WO00/02049

PCT Pub. Date: Jan. 13, 2000

(30) Foreign Application Priority Data

| Jul. 1, 1998 | (JP) | 10-186624 |
| Jul. 1, 1998 | (JP) | 10-186628 |
| Jul. 1, 1998 | (JP) | 10-186636 |
| Jul. 1, 1998 | (JP) | 10-186640 |
| Jul. 7, 1998 | (JP) | 10-191981 |
| Jul. 7, 1998 | (JP) | 10-192052 |
| Jul. 7, 1998 | (JP) | 10-192114 |
| Jul. 7, 1998 | (JP) | 10-192150 |
| Jul. 7, 1998 | (JP) | 10-192151 |
| Jan. 14, 1999 | (JP) | 11-008064 |
| Feb. 1, 1999 | (JP) | 11-024285 |
| Feb. 1, 1999 | (JP) | 11-024286 |

(51) Int. Cl.⁷ .......................................... G01N 35/533
(52) U.S. Cl. .................. 436/518; 436/523; 436/525; 436/528; 436/535; 436/808; 435/7.1; 435/7.94; 435/7.92; 435/7.5; 435/4
(58) Field of Search .................. 436/518, 523, 436/525, 528, 535, 808; 435/7.1, 7.94, 7.92, 7.5, 4

(56) References Cited

U.S. PATENT DOCUMENTS

| 4,632,901 A | * | 12/1986 | Valkirs et al. |
| 5,160,701 A | * | 11/1992 | Brown, III et al. |
| 5,567,591 A | * | 10/1996 | Lovell et al. |
| 5,876,944 A | * | 3/1999 | Kuo |

FOREIGN PATENT DOCUMENTS

| EP | 0813064 A1 | 12/1997 |
| JP | A 3-46561 | 2/1991 |
| JP | A 4-66871 | 3/1992 |
| JP | A 6-130063 | 5/1994 |
| JP | A 8-29422 | 2/1996 |
| JP | A 8-29442 | 2/1996 |
| JP | A 9-145710 | 6/1997 |

* cited by examiner

Primary Examiner—Christopher L. Chin
Assistant Examiner—Pensee T. Do
(74) Attorney, Agent, or Firm—Birch, Stewart, Kolasch & Birch, LLP

(57) ABSTRACT

The present invention relates to an immunological detection method capable of performing detection of an analyte in a test sample, and a kit used therefor. There is provided an immunological detection method for detecting an analyte by using a water-absorbent substrate in which a capture region is positioned in a given region on a surface thereof, the capture region being immobilized with a first immunochemical component capable of specifically binding to the analyte, wherein the detection signal is amplified and a kit used therefor.

14 Claims, 15 Drawing Sheets

A

B

C

D

E

IMMUNOLOGIC TEST METHOD AND IMMUNOLOGIC TEST KIT

This application is the national phase under 35 U.S.C. §371 of PCT International Application No. PCT/JP99/03539 which has an International filing date of Jun. 30, 1999, which designated the United States of America.

TECHNICAL FIELD

The present invention relates to an immunological detection method capable of performing detection of an analyte in a test sample and a kit used therefor. More particularly, the present invention relates to immunochromatography comprising the step of amplifying a detection signal.

BACKGROUND ART

In an immunological analysis of a biological sample, or the like, a method for carrying out its detection quickly and simply includes immunochromatography. This method generally comprises the steps as described below. Concretely, when a mixture comprising a liquid of a test sample and a labeled antibody capable of specifically binding to an analyte is absorbed and developed from one end of a test strip comprising a water-absorbent substrate having a capture region immobilized with an antibody capable of specifically binding to the analyte, a labeled antibody-analyte complex formed in the mixture is bound to the immobilized antibody, thereby capturing the complex on the capture region. Therefore, the analyte in the liquid of a test sample can be determined by assaying the labeled antibody bound to the capture region.

In addition, as a method for obtaining a detection signal by the immunochromatography mentioned above with a higher sensitivity, a method using two kinds of labeled antibodies is disclosed in Japanese Patent Laid-Open No. Hei 10-062419. In other words, the construction is such that a first labeled antibody and a second labeled antibody are respectively positioned (absorbed) as reagent regions between a capture region (immobilized with another antibody capable of specifically binding to the analyte) and a site at which a test sample is absorbed in the test strip, wherein the first labeled antibody is obtained by labeling an antibody capable of specifically binding to an analyte, and the second labeled antibody is obtained by labeling a secondary antibody capable of specifically binding to the antibody. The analyte in the sample forms a complex with the first labeled antibody, and thereafter the second labeled antibody is further bound to the first labeled antibody, thereby forming a complex of [analyte-first labeled antibody-second labeled antibody]. The immunological complex is captured by an antibody immobilized on the capture region. Therefore, a signal amplified by the second labeled antibody is detected on the capture region.

However, at present, a sufficient detection sensitivity has not yet been obtained even by the signal-amplifying immunochromatography described above. Further, when a test sample is feces, urine, blood, or the like, there is necessitated additional procedures such as a step of suspending a sample in an appropriate buffer as a pretreatment and/or partial purification process comprising separating and removing heterogeneous substances in the test sample, so that it has a defect of lack of quickness.

Accordingly, an object of the present invention is to provide an immunological detection method relating to immunochromatography, the method capable of detecting an analyte more quickly and with high sensitivity, and a kit used therefor.

DISCLOSURE OF INVENTION

The present invention provides the following immunological detection methods and kits used therefor:

[1] an immunological detection method for detecting an analyte by using a water-absorbent substrate in which a capture region immobilized with a first immunochemical component capable of specifically binding to the analyte is positioned in a given region on a surface thereof, wherein the immunological detection method is characterized by the use of:

(1) a solution comprising a labeled immunochemical component (first labeled immunochemical component) comprising a second immunochemical component capable of specifically binding to the analyte and a labeling substance, wherein the labeling substance is bound to the second immunochemical component; and (2) a solution comprising a labeled immunochemical component (second labeled immunochemical component) comprising a third immunochemical component capable of specifically binding to the second immunochemical component and a labeling substance, wherein the labeling substance is bound to the third immunochemical component;

[2] an immunological detection method comprising forming on a capture region an immunological complex in which an analyte in a test sample is sandwiched with a first immunochemical component capable of specifically binding to the analyte, and a labeled component (first labeled component), the first labeled component comprising a second immunochemical component capable of specifically binding to the analyte, a third immunochemical component incapable of binding to the analyte and a labeling substance, wherein the labeling substance is bound to the second and third immunochemical components, wherein the first immunochemical component is immobilized on the capture region positioned in a given region on a surface of a water-absorbent substrate; and determining a signal of the labeling substance on the capture region, characterized in that the method comprises forming an immunological complex in which a labeled component (second labeled component) is bound to the third immunochemical component present in a sandwiched immunological complex via a mediating substance, the second labeled component comprising a fourth immunochemical component capable of specifically binding to the third immunochemical component via the mediating substance, and a labeling substance, wherein the labeling substance is bound to the fourth immunochemical component, thereby amplifying the signal of the labeling substance;

[3] a sandwiched-type immunological detection method wherein at a capture region immobilized with a first immunochemical component capable of binding to an analyte, the analyte is sandwiched by the first immunochemical component and a labeled component comprising a second immunochemical component capable of binding to the analyte and a labeling substance, wherein the labeling substance is bound to the second immunochemical component, characterized in that the immunological detection method comprises forming a complex via binding between a biotin and an avidin, and detecting the analyte;

[4] a kit for immunological detection characterized in that the kit comprises a water-absorbent substrate in which a capture region immobilized with a first immunochemical component capable of specifically binding to an analyte is positioned in a given region on a surface thereof; a labeled immunochemical component (first labeled immunochemical component), the first labeled immunochemical component comprising a second immunochemical component capable of specifically binding to the analyte, and a labeling substance, wherein the labeling substance is bound to the second immunochemical component; and a labeled immunochemical component (second labeled immunochemical component), the second labeled immunochemical component comprising a third immunochemical component capable of specifically binding to the second immunochemical component, and a labeling substance, wherein the labeling substance is bound to the third immunochemical component;

[5] a kit for immunological detection comprising a water-absorbent substrate in which a capture region immobilized with a first immunochemical component capable of specifically binding to an analyte is positioned in a given region on a surface thereof; a labeled component (first labeled component), the first labeled immunochemical component comprising a second immunochemical component capable of specifically binding to the analyte, a third immunochemical component incapable of binding to the analyte, and a labeling substance, wherein the labeling substance is bound to the second and third immunochemical components; a labeled component (second labeled component), the second labeled component comprising a fourth immunochemical component capable of specifically binding to the third immunochemical component via a mediating substance, and a labeling substance, wherein the labeling substance is bound to the fourth immunochemical component; and a mediating substance for mediating binding of the third and fourth immunochemical components;

[6] a kit for immunological detection comprising an immunological test strip comprising a capture region immobilized with a first immunochemical component capable of binding to an analyte on a water-absorbent substrate; a labeled component comprising a labeling substance, a biotin and a second immunochemical component capable of binding to the analyte, wherein the labeling substance is bound to the biotin and the second immunochemical component; and an avidin;

[7] a kit for immunological detection comprising an immunological test strip comprising a capture region immobilized with a first immunochemical component capable of binding to an analyte on a water-absorbent substrate; a labeled component comprising a first labeling substance, and an avidin and a second immunochemical component capable of binding to the analyte, wherein the labeling substance is bound to the avidin and the second immunochemical component; and a conjugate comprising a biotin and a second labeling substance; and

[8] a kit for immunological detection comprising an immunological test strip comprising a capture region immobilized with a first immunochemical component capable of binding to an analyte on a water-absorbent substrate; a labeled component comprising a first labeling substance, and a biotin and a second immunochemical component capable of binding to the analyte, wherein the first labeling substance is bound to a biotin and the second immunochemical component; and a conjugate comprising an avidin and a second labeling substance.

BRIEF DESCRIPTION OF THE DRAWINGS

FIG. 1 is a schematic view explaining the principle of the immunological detection method of the present invention (Embodiment A-1), wherein FIG. 1A: Formation of an immunological complex in a mixture comprising a liquid of a test sample and a solution of a first labeled immunochemical component;

FIG. 1B: Absorption and development of the mixture comprising a liquid of a test sample and a solution of a first labeled immunochemical component to a test strip;

FIG. 1C: Capture of an analyte on a capture region;

FIG. 1D: Absorption and development of a solution of a second labeled immunochemical component to a test strip; and FIG. 1E: Amplification of a detection signal by binding of the second labeled immunochemical component to the capture region.

FIG. 2 is a schematic view explaining the principle of the immunological detection method of the present invention (Embodiment A-2), wherein FIG. 2A: Formation of an immunological complex in a mixture comprising a liquid of a test sample, a solution of a first labeled immunochemical component and a solution of a second labeled immunochemical component;

FIG. 2B: Absorption and development of the mixture comprising a liquid of a test sample, a solution of a first labeled immunochemical component and a solution of a second labeled immunochemical component to a test strip;

FIG. 2C: Capture of an analyte and amplification of a detection signal on a capture region.

FIG. 3 is a schematic view explaining the principle of the immunological detection method of the present invention (Embodiment A-3), wherein FIG. 3A: Application of a test sample to a test strip, and absorption and development of a solution of a first labeled immunochemical component to a test strip;

FIG. 3B: Formation of a complex comprising a first labeled immunochemical component and an analyte in a test sample;

FIG. 3C: Capture of an analyte on a capture region;

FIG. 3D: Absorption and development of a solution of a second labeled immunochemical component to a test strip; and FIG. 3E: Binding of the second labeled immunochemical component to the capture region and amplification of a detection signal.

FIG. 4 is a schematic view explaining the principle of the immunological detection method of the present invention (Embodiment A-4), wherein FIG. 4A: Application of a test sample to a test strip, and absorption and development of a mixture comprising a first labeled immunochemical component and a second labeled immunochemical component to a test strip;

FIG. 4B: Formation of an immunological complex comprising an analyte in a test sample, a first labeled immunochemical component and a second labeled immunochemical component; and FIG. 4C: Capture of the labeled immunological complex and amplification of a detection signal on a capture region.

Incidentally, the numerals in the figures are given for each drawing.

BEST MODE FOR CARRYING OUT THE INVENTION

In the immunological detection method of the present invention, there are three kinds of embodiments (Embodiment A, Embodiment B and Embodiment C). The terminologies in each of the embodiments are in principle understood to have the meanings as defined in each of the embodiments.

[1] Embodiment A

Embodiment A is an immunological detection method for detecting an analyte by using a water-absorbent substrate in which a capture region immobilized with a first immunochemical component capable of specifically binding to the analyte is positioned in a given region on a surface thereof, wherein the immunological detection method is characterized by the use of:

(1) a solution comprising a labeled immunochemical component (first labeled immunochemical component) comprising a second immunochemical component capable of specifically binding to the analyte and a labeling substance, wherein the labeling substance is bound to the second immunochemical component; and (2) a solution comprising a labeled immunochemical component (second labeled immunochemical component) comprising a third immunochemical component capable of specifically binding to the second immunochemical component and a labeling substance, wherein the labeling substance is bound to the third immunochemical component.

When this embodiment is carried out, there are the following four embodiments.

1) Embodiment A-1

Figure 1:
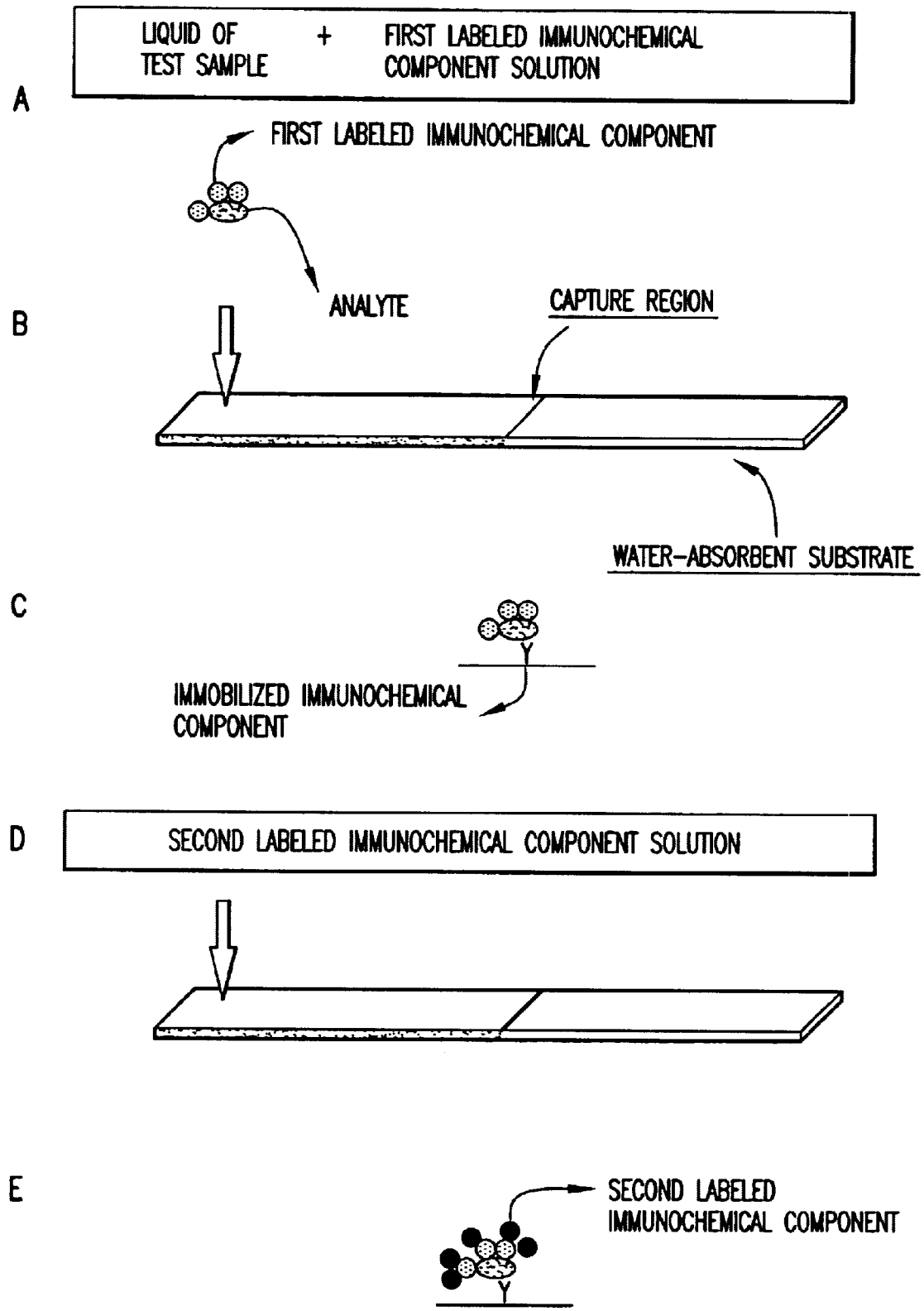

(1) When a liquid of a test sample to be detected and a solution comprising a first labeled immunochemical component are mixed, an analyte contained in the liquid of a test sample is bound to the first labeled immunochemical component, thereby forming an immunological complex comprising the first labeled immunochemical component and the analyte (FIG. 1A). From one end of a water-absorbent substrate, when the above mixture is absorbed and then developed, the above immunological complex formed in the mixture migrates in the water-absorbent substrate along with the migration of the solutions (FIG. 1B).

(2) The migrated immunological complex is further bound on a capture region to a first immunochemical component immobilized at the capture region, and a labeled immunological complex of first labeled immunochemical component-analyte-first immunochemical component is newly formed, thereby capturing the immunological complex on the capture region (FIG. 1C).

(3) From one end of the above water-absorbent substrate, when a solution comprising a second labeled immunochemical component is absorbed and developed, the second labeled immunochemical component migrates in the water-absorbent substrate along with the migration of the solutions (FIG. 1D). The second labeled immunochemical component reaching to the capture region is bound to the first labeled immunochemical component in the above labeled immunological complex formed on the capture region, thereby forming a double-labeled immunological complex of second labeled immunochemical component-first labeled immunochemical component-analyte-first immunochemical component (FIG. 1E).

(4) By capturing the double-labeled immunological complex at the capture region as described above, the labeled substances are assembled at one place and bound to amplify a detection signal, thereby making it possible to detect the presence of the analyte at a higher sensitivity, the labeled substances constituting first and second labeled immunochemical components (FIG. 1E).

2) Embodiment A-2

Figure 2:
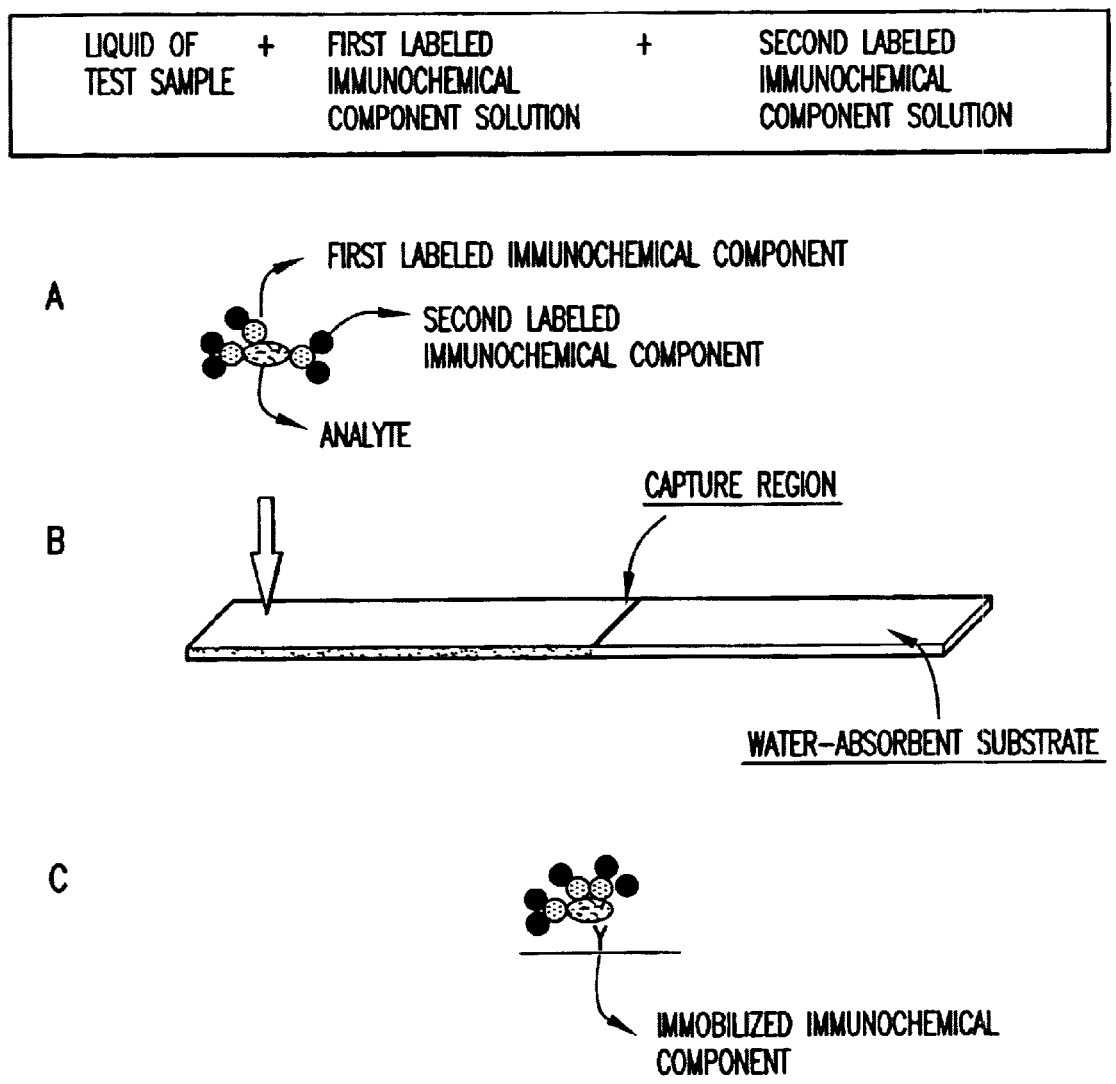

(1) When a liquid of a test sample to be detected, a solution comprising a first labeled immunochemical component and a solution comprising a second labeled immunochemical component are mixed, an analyte contained in the liquid of a test sample is bound to the first labeled immunochemical component, and the second labeled immunochemical component is further bound to the first labeled immunochemical component, thereby forming a double-labeled immunological complex (FIG. 2A). From one end of a water-absorbent substrate, when the above mixture is absorbed and then developed, the above immunological complex formed in the mixture migrates in the water-absorbent substrate along with the migration of the solutions (FIG. 2B).

(2) The migrated immunological complex is further bound on a capture region to a first immunochemical component immobilized at a capture region, and a labeled immunological complex of second labeled immunochemical component-first labeled immunochemical component-analyte-first immunochemical component is newly formed, thereby capturing the immunological complex on the capture region (FIG. 2C).

(3) By capturing the labeled immunological complex at the capture region as described above, the labeled substances are assembled at one place and bound to amplify a detection signal, thereby making it possible to detect the presence of the analyte at a higher sensitivity, the labeled substances constituting first and second labeled immunochemical components (FIG. 2C).

3) Embodiment A-3

Figure 3:
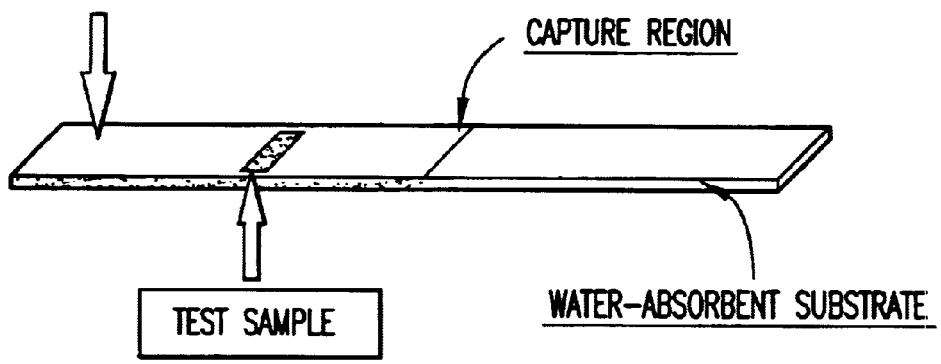
Figure 3:
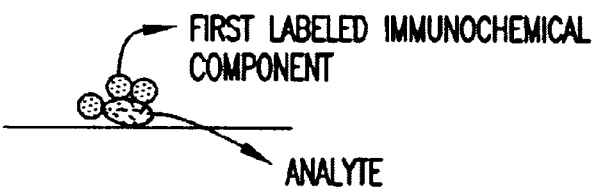
Figure 3:
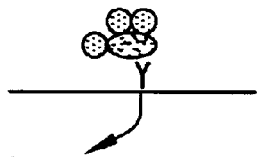
Figure 3:
Figure 3:
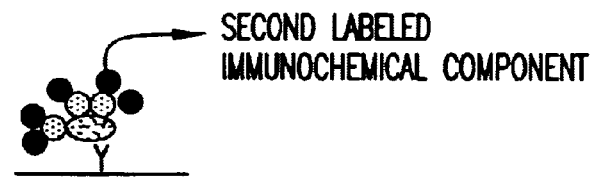

(1) A test sample to be detected is absorbed or applied on a front side of a capture region (FIG. 3A).

(2) From one end (the end closer to a portion at which the test sample is absorbed or applied than the capture region) of the water-absorbent substrate (FIG. 3A), when a solution comprising a first labeled immunochemical component is absorbed and then developed, the first labeled immunochemical component migrates in the water-absorbent substrate along with the migration of the solution, and is bound to an analyte in the test sample, thereby forming an immunological complex (FIG. 3B).

(3) The migrated immunological complex is further bound on a capture region to a first immunochemical component immobilized at a capture region, and an immunological complex of first labeled immunochemical component-analyte-first immunochemical component is newly formed, thereby capturing the immunological complex on the capture region (FIG. 3C).

(4) From one end of the above water-absorbent substrate (FIG. 3D), when a solution comprising a second labeled immunochemical component is further absorbed and then developed, the second labeled immunochemical component migrates in the water-absorbent substrate along with the migration of the solution, thereby binding to the first labeled immunochemical component of the immunological complex captured on the capture region (FIG. 3E).

(5) By capturing the complex at the capture region as described above, the labeled substances are assembled at one place and bound to amplify a detection signal, thereby making it possible to detect the presence of the analyte at a higher sensitivity, the labeled substances constituting first and second labeled immunochemical components (FIG. 3E).

4) Embodiment A-4

Figure 4:
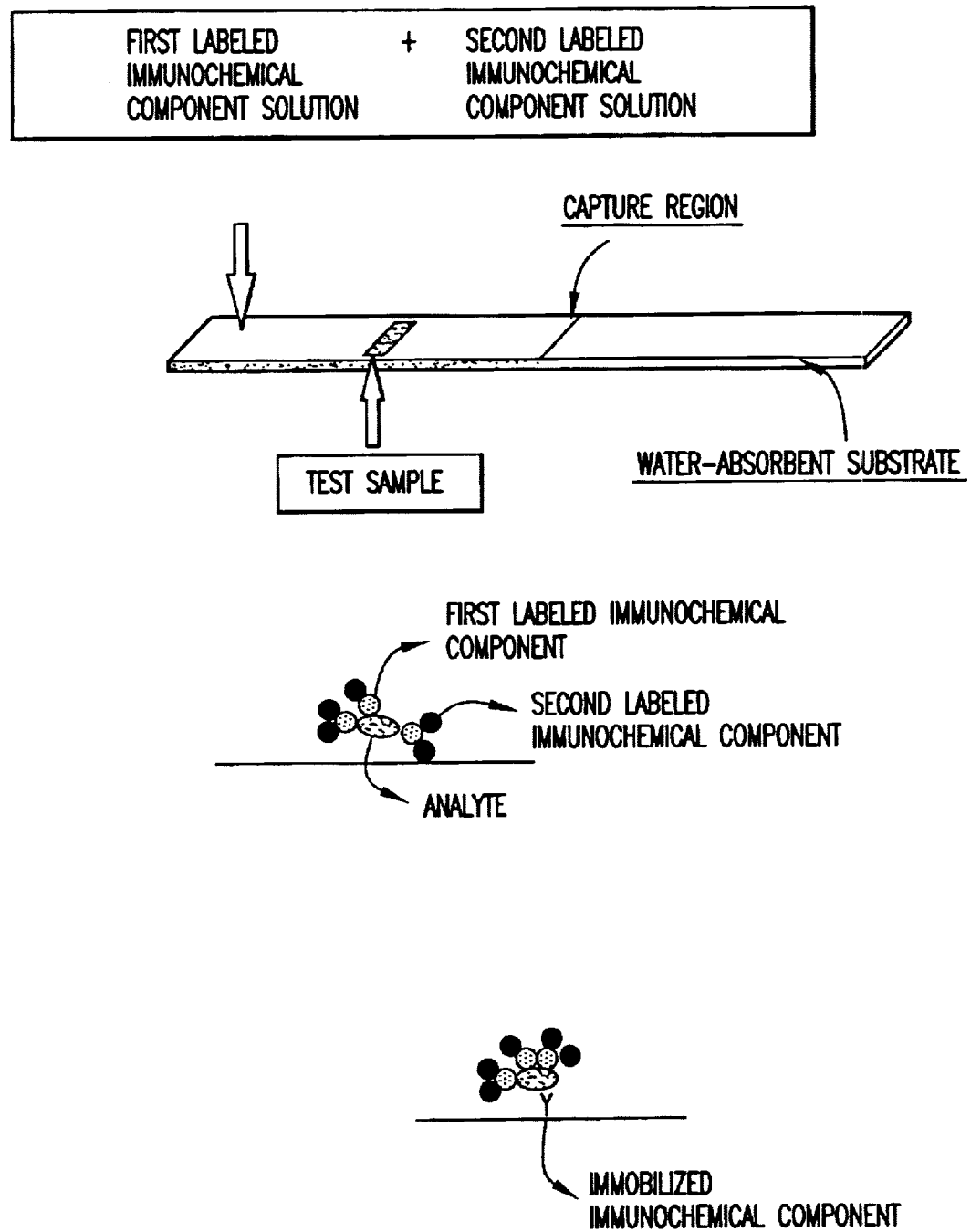

(1) A test sample to be detected is absorbed or applied on a front side of a capture region (FIG. 4A).

(2) From one end (the end closer to a portion at which the test sample is absorbed or applied than the capture region) of the water-absorbent substrate, when a mixture comprising:

a solution comprising a first labeled immunochemical component and a solution comprising a second labeled immunochemical component is absorbed and then developed (FIG. 4A), the first and second labeled immunochemical components migrate in the water-absorbent substrate along with the migration of the solutions, and are bound to the analyte in the test sample, thereby forming a double-labeled immunological complex (FIG. 4B).

(3) The migrated immunological complex is further bound on a capture region to a first immunochemical component immobilized at a capture region, and an immunological complex of second labeled immunochemical component-first labeled immunochemical component-analyte-first immunochemical component is newly formed, thereby capturing the immunological complex on the capture region (FIG. 4C).

(4) By capturing the immunological complex at the capture region as described above, the labeled substances are assembled at one place and bound to amplify a detection signal, thereby making it possible to detect the presence of the analyte at a higher sensitivity, the labeled substances constituting first and second labeled immunochemical components (FIG. 4C).

The analyte which can be detected by the method of this Embodiment A is not particularly limited, as long as it is those capable of forming a sandwiched immunological complex by binding to the first immunochemical component and the second immunochemical component via immunochemical reaction (i.e. antigen-antibody reaction). The analyte includes, for instance, bacteria and constituents thereof; bacteria-bearing toxins; proteins (for instance, microbial constitutive proteins such as surface antigens); antigenic peptides such as tumor marker antigens in biological samples; viral antigens and antibodies; mycoplasma; actinomycetes; yeasts; and molds. The bacteria and constituents thereof include, for instance, *Escherichia coli* O157, Salmonella, Staphylococcus (including, for instance, drug-resistant bacteria such as methicillin resistant *Staphylococcus aureus*), hemolytic streptococcus, Campylobacer, *Clostridium perfringens, Vibrio parahaemolyticus, Helicobacter pylori, Chlamydia trachomatis*, constituents thereof, and the like. The bacteria-bearing toxin includes, for instance, Vero toxin, streptolysin O, and the like. The protein includes, for instance, human transferrin, human albumin, human immunoglobulin, microglobulin and C-reactive proteins, and the like. The viral antigens and antibodies include HBc, HBe and HBs antigens and antibodies from hepatitis B virus; antigens and antibodies from hepatitis C virus; human immunodeficient viral antigens and antibodies; rotavirus antigens and antibodies; adenovirus antigens and antibodies, and the like.

In the method of the present invention, each of the first immunochemical component immobilized to a capture region, and the second immunochemical component used as a first labeled immunochemical component is not particularly limited, as long as it is a substance capable of specifically binding to an analyte via antigen-antibody reaction. If the analyte is an antigen (for instance, a protein, a peptide, a haptene, or the like), the first and second immunochemical components are antibodies each capable of specifically binding to the antigen. The antibody may be a monoclonal antibody or a polyclonal antibody. In addition, the antibody in the present invention is intended to encompass a fragment of an antibody possessing specific affinity to an analyte, including, for instance, H chain, L chain, Fab, F(ab')$_2$, V$_H$, V$_L$, and the like. On the other hand, when the analyte is an antibody, each of the first and second immunochemical components is an antigen capable of specifically binding to each of the antibody, or secondary antibody capable of specifically binding to the antibody as an antigen. As the first immunochemical component and the second immunochemical component, those by themselves of known ones used in the sandwich method may be appropriately selected depending upon the analyte. In addition, if each of the immunochemical components is an antibody, the components can also be prepared with the isolated analyte as a sensitized antigen by using a known antibody preparation technique. When all of the first, second and third immunochemical components are antibodies, although the first antibody and the second antibody differ depending upon the kinds of the antibody used and the analyte, there can be used two kinds of antibodies recognizing an identical antigenic determinant, or two kinds of antibodies recognizing different antigenic determinants. More preferably, those recognizing different antigenic determinants can be used.

The third immunochemical component used as a second labeled immunochemical component is an immunochemical component specifically binding to the second immunochemical component in the first labeled immunochemical component wherein the immunochemical component is incapable of binding to the immobilized first immunochemical component. As the third immunochemical component, those conventionally known to be used as a secondary antibody by indirect immunoassay can be appropriately selected. In addition, it can be prepared by using a known antibody preparation technique with the second immunochemical component as a sensitized antigen. When all of the first, second and third immunochemical components are antibodies and an anti-IgG antibody is used as a third antibody, it is preferable that the origins of the animals from which a first antibody and a second antibody are derived are different from each other.

The water-absorbent substrate usable for the present invention is not particularly limited, as long as it can absorb a test sample comprising an analyte, including, for instance, a liquid sample such as a solution extracted from foods, culture supernatant thereof, feces suspension (solution), plasma, sera, blood, urine or saliva, or a dilution prepared by diluting these liquid samples with an appropriate buffer, and solutions each comprising a first labeled immunochemical component and a second labeled immunochemical component. In the present invention, preferably used is the water-absorbent substrate which can secure a time period for sufficiently carrying out a reaction of the analyte in a test sample with labeled immunochemical components or with a first immunochemical component immobilized to a capture region.

When the water-absorbent substrate has poor water absorbency, a long period of time is required for a test sample in order to reach the capture region as described below, and consequently a quick assay cannot be taken. On the other hand, when the water-absorbent substrate has exceeding high water absorbency, a time period required for sufficiently carrying out the reaction of an analyte in a test sample with labeled immunochemical components or a first immunochemical component of the capture region is deficient, thereby making it difficult to carry out an accurate assay.

Therefore, a preferable extent of the water absorbency of the water-absorbent substrate in the present invention is such that a water absorption distance after 1 minute from immersing one end of the water-absorbent substrate cut in rectangles of 5 mm width is about 0.5 to about 5 cm.

Preferable concrete examples of the water-absorbent substrate of the present invention include nonwoven fabrics, filter paper, glass fiber fabrics, glass filters, nitrocellulose filters, porous materials, and the like. These substrates have the advantages that these substrates have an appropriate water absorbing ratio, and that if the labeling substance is colored particles, when the labeling substance is bound to the colored particles and thereby color is developed, these substrates have excellent visual confirmability.

In addition, in order to adjust the water absorbency of these substrates, the surface of the substrate is coated or impregnated with a hydrophilic polymer or a surfactant. Further, in the present invention, as the water-absorbent substrate, a substrate made of the homogeneous material may be used, or a continuous substrate obtained by bonding those made of heterogeneous materials by a given bonding means can be used.

In the present invention, the shape of the water-absorbent substrate is not particularly limited, as long as the shape is a shape capable of developing a test sample. For instance, those of rectangular sheet-like (strip-like) or rod-like forms are preferable.

In the present invention, a capture region means a region in which a first immunochemical component capable of binding to an analyte is immobilized on a water-absorbent substrate. A method for immobilizing a first immunochemical component on a water-absorbent substrate (a method for preparing a capture region) is not particularly limited, and methods for immobilizing by conventionally known physical adsorption method and covalent bonding method are preferable. In particular, from the viewpoint that the immunochemical components are less likely to be released from the substrate, a method for immobilizing by covalent bonding method is preferable. When the water-absorbent substrate does not have a functional group for the above covalent bonding method, a substrate is prepared by, for instance, using a polymer having an appropriate functional group, and thereafter the components are attached to the water-absorbent substrate to an extent so as not to inhibit the water-absorbency of the water-absorbent substrate. Alternatively, a capture region can be also prepared by applying to a water-absorbent substrate a solution comprising a first immunochemical component and a hydrophilic polymer, and thereafter immersing in a solidifying agent for solidifying the above hydrophilic polymer. As the above hydrophilic polymer, there can be used hydroxypropyl methyl cellulose, a polyvinyl alcohol, hydroxyethyl cellulose, or the like. In addition, as the solidifying agent, there can be used acetone, ethanol, methanol, an ether, or the like.

In the present invention, the distance between the above capture region and the site at which absorption of a mixture and a solution comprising a second labeled immunochemical component is initiated (hereinafter referred to as solution-absorbing site), the mixture comprising a liquid of a test sample and a solution comprising a first labeled immunochemical component, is not particularly limited, and the distance is preferably from 1 to 6 cm, more preferably from 3 to 4 cm or so. When the distance is too far, there are undesirably likely to cause such problems that the test sample does not reach to the capture region, that the sensitivity of the detection signal becomes too strong, or that a long period of time is necessary for assaying. On the other hand, when the distance is too close, there are undesirably like to cause such problems that the coloring in the capture region is not homogeneous, but becomes uneven, or that the sensitivity of the detection signal becomes too low.

The solution-absorbing site is not particularly limited, as long as it does not prevent of a solution comprising a test sample or each of labeled immunochemical components from migrating onto the water-absorbent substrate, and it may also serve as a substrate, or it may be those prepared by newly gluing a nonwoven fabric, a woven fabric, or the like to the water-absorbent substrate. In the present invention, the water-absorbent substrate comprising a capture region and a solution-absorbing site, wherein a first immunochemical component capable of specifically binding to an analyte is immobilized to the capture region, may be hereinafter referred to as "an immunological test strip of the present invention," or simply "test strip" in some cases.

The first labeled immunochemical component in the method of the present invention comprises an immunochemical component (second immunochemical component) capable of specifically binding to an analyte, and a labeling substance, wherein the labeling substance is bound to the second immunochemical component. Alternatively, the second labeled immunochemical component comprises an immunochemical component (third immunochemical component) capable of specifically binding to the second immunochemical component, and a labeled substance, wherein the labeling substance is bound to the third immunochemical component. The labeling substance used herein may be any labeling substances conventionally used in immunochemical assay. Examples thereof include colored particles; enzymes, such as alkali phosphatases and peroxidases; fluorescent substances, such as FITC and rhodamine, and the like. In order to achieve highly efficient amplification of the detection signal, it is preferable that the labeling substances used in the first and second labeled immunochemical components are identical. In the method of the present invention, from the aspect of carrying out a quick detection, the colored particles are preferably used as a labeling substance. The colored particles are not particularly limited, as long as they can be visually detected. There can be used, for instance, colloidal particles comprising metals such as gold, silver and copper; colored latex prepared by coloring latex with pigments and dyes represented by Sudan Blue or Sudan Red IV, Sudan III, Oil Orange, Quinizaline Green, or the like. From the aspect of the visual confirmability, it is preferable to use gold colloid or colored latex colored in blue, red, green or orange. In addition, in consideration of such aspects as the dispersion stability and the ease in adjustment of the detection sensitivity of an analyte, it is more desirable to use colored latex comprising water-dispersible polymeric particles colored in blue, red, or the like.

The particle size of the colored particles is not particularly limited, as long as the colored particles have excellent coloring during detection and have mobility in the substrate to an extent that the water absorbency of the water-absorbent substrate is not lowered. From the aspects of the storage stability and the ease in preparation, the particle size is exemplified in ranges of preferably from 0.01 to 5 $\mu$m, more preferably from 0.01 to 3 $\mu$m, more preferably from 0.05 to 3 $\mu$m, particularly preferably from 0.05 to 0.5 $\mu$m. When the particle size is too small, the degree of coloring for one particle is small, so that the degree of coloring even when bound to a capture region is poor, thereby having poor visual confirmability. On the other hand, when the particle size is too large, the clogging to the water-absorbent substrate takes place by slightly agglomerating the colored particles and non-specific coloring is likely to be caused.

As the method for labeling immunochemical components with the colored particles described above, there can be used conventionally known methods, including, for instance, covalent bonding method, physical adsorption method, ionic bonding method, and the like. From the aspect that the colored particles are not released from the immunochemical components and thus being stable, the covalent bonding method is more preferably used.

In the method of the present invention, in order to detect a plurality of analytes in a test sample, a corresponding plurality of immunochemical components can be labeled with separate colored particles, and the colored particles usable herein may have an identical color or different colors. When the colored particles having an identical color are used, it is desired that the colored particles are positioned in a distance apart to an extent that a capture region to which each of immunochemical components capable of specifically binding to each analyte is immobilized can be distinguished.

When the labeling substance is an enzyme or a fluorescent substance, as the detection of the labeling substance in the capture region, conventionally used detection means by EIA or fluorescent antibody method (FIA) can be appropriately selected.

The solution comprising a first labeled immunochemical component and the solution comprising a second labeled immunochemical component can be prepared by dispersing (dissolving) each labeled immunochemical component in an appropriate dispersant (solvent). The dispersant for dispersing the labeled immunochemical components is not particularly limited, as long as it does not inhibit an antigen-antibody reaction between an analyte and a first labeled immunochemical component, and that between the first labeled immunochemical component and a second labeled immunochemical component. Preferably, a buffer, including, for instance, phosphate buffer, acetate buffer, borate buffer, Tris-HCl buffer or the like can be appropriately selected to be used, the buffer having appropriate pH and salt concentration for an antigen-antibody reaction. The concentration of each labeled immunochemical component during the signal detection is in the range of from 0.005 to 5%, preferably from 0.01 to 0.5%. When the concentration is too low, the number of particles bound to the capture region is small, so that the detection sensitivity becomes poor. In addition, when the concentration is too high, it is not only economically disadvantageous but also there arise problems that excessive labeling substances remain on parts other than the capture region, thereby making the signal in the capture region unclear. Incidentally, the solution comprising a labeled immunochemical component is simply referred to as a labeled immunochemical component solution.

The kit for immunological detection of the present invention usable for Embodiment A can be preferably used in the immunological detection method of the present invention. The kit at least comprises the following ingredients:

(a) a water-absorbent substrate in which a capture region immobilized with a first immunochemical component capable of specifically binding to an analyte is positioned in a given region on a surface thereof;

(b) a labeled immunochemical component (first labeled immunochemical component), the first labeled immunochemical component comprising a second immunochemical component capable of specifically binding to the analyte, and a labeling substance, wherein the labeling substance is bound to the second immunochemical component; and (c) a labeled immunochemical component (second labeled immunochemical component), the second labeled immunochemical component comprising a third immunochemical component capable of specifically binding to the second immunochemical component, and a labeling substance, wherein the labeling substance is bound to the third immunochemical component.

The preferred embodiments of the water-absorbent substrate and the first and second labeled immunochemical components are those preferably usable for the immunological detection method of the present invention as described above.

The kit of the present invention may further comprise additional ingredients which can be preferably used in the immunological detection method of the present invention in addition to the ingredients described above. For instance, there are cited the above buffers preferably usable for dispersing the first and second labeled immunochemical components.

In Embodiment A-1, since in the immunochromatography using the kit of the present invention, first an analyte and a first labeled immunochemical component are previously bound to a capture region, and thereafter a second labeled immunochemical component is bound thereto, problems in detection can be avoided which can take place in conventional methods that the binding efficiency of the analyte with the first immunochemical component immobilized to a capture region, namely the capturing ratio of the analyte in the capture region, is lowered owing to steric hindrance of two kinds of the labeled immunochemical components, or that clogging of the immunological complex comprising the two kinds of the labeled immunochemical components takes place on the water-absorbent substrate.

In Embodiment A-2, since in the immunochromatography using the kit of the present invention, a liquid of a test sample is previously mixed with a first labeled immunochemical component and a second labeled immunochemical component, and thereafter developed on a test strip, a sufficient period of time is secured for the formation of a double-labeled immunological complex of [analyte-first labeled immunochemical component-second labeled immunochemical component]. Therefore, problems in detection can be avoided which can take place in conventional methods that amplification of the detection signal is insufficient because an analyte is captured on a capture region without being doubly labeled.

In Embodiment A-3, in the immunochromatography using the kit of the present invention, a test sample is previously absorbed or applied on a test strip, and a first labeled immunochemical component solution is firstly developed thereon, thereby capturing a formed immunological complex comprising an analyte and a first labeled immunochemical component by an immunochemical component specific to the analyte, the immunochemical component being immobilized to a capture region; and thereafter, a second labeled immunochemical component solution is further developed on a test strip, thereby binding the immunological complex captured on the capture region to the second labeled immunochemical component. Therefore, problems in detection can be avoided which can take place in the conventional methods such as steric hindrance by two kinds of the labeled immunochemical components and clogging of the immunological complex, and consequently, the analyte can be detected at a higher sensitivity. In addition, according to this method, since the pretreatment of the test sample is not necessitated, a time period required for detection can be shortened than that of a conventional method.

In Embodiment A-4, since in the immunochromatography using the kit of the present invention, the first labeled immunochemical component and the second labeled immunochemical component are previously mixed, and thereafter developed on a test strip, a sufficient period of time is secured for the formation of a double-labeled immunological complex of [analyte-first labeled immunochemical component-second labeled immunochemical component]. Therefore, problems in detection can be avoided which can take place in conventional methods that amplification of the detection signal is insufficient because an analyte is captured on a capture region without being doubly labeled, and consequently, the analyte can be detected at a higher sensitivity. In addition, according to this method, since the pretreatment of the test sample is not necessitated, a time period required for detection can be shortened than a conventional method, so that more quick detection of the analyte can be made.

[2] Embodiment B

Embodiment B is an immunological detection method comprising forming on a capture region an immunological complex in which an analyte in a test sample is sandwiched with a first immunochemical component capable of specifically binding to the analyte, and a labeled component (first labeled component), the first labeled component comprising a second immunochemical component capable of specifically binding to the analyte, a third immunochemical component incapable of binding to the analyte and a labeling substance, wherein the labeling substance is bound to the second and third immunochemical components, wherein the first immunochemical component is immobilized on the capture region positioned in a given region on a surface of a water-absorbent substrate; and determining a signal of the labeling substance on the capture region, characterized in that the method comprises forming an immunological complex in which a labeled component (second labeled component) is bound to the third immunochemical component present in a sandwiched immunological complex via a mediating substance, the second labeled component comprising a fourth immunochemical component capable of specifically binding to the third immunochemical component via the mediating substance, and a labeling substance, wherein the labeling substance is bound to the fourth immunochemical component, thereby amplifying the signal of the labeling substance.

When this embodiment is carried out, there are the following five embodiments.

1) Embodiment B-1

An immunological detection method, characterized in that the method comprises the following steps:

(1) from one end, closer to a reagent region than a capture region, of a water-absorbent substrate, wherein the capture region immobilized with a first immunochemical component capable of specifically binding to an analyte, and a reagent region maintained in a form capable of releasing by contact with water a labeled component (first labeled component), the first labeled component comprising a second immunochemical component capable of specifically binding to the analyte, a third immunochemical component incapable of binding to the analyte and a labeling substance, wherein the labeling substance is bound to the second and third immunochemical components, are positioned in a given region on a surface thereof, developing a mixture comprising:

a solution comprising a test sample;

a solution comprising a labeled component (second labeled component), the second labeled component comprising a fourth immunochemical component capable of specifically binding to the third immunochemical component via a mediating substance, and a labeling substance, wherein the labeling substance is bound to the fourth immunochemical component; and a solution comprising the mediating substance;

(2) binding an immunological complex comprising the analyte, the first labeled component, the mediating substance and the second labeled component to the first immunochemical component immobilized at the capture region, wherein the immunological complex is formed on the water-absorbent substrate, thereby capturing the immunological complex; and (3) thereafter detecting the analyte by determining a signal of the labeling substance on the capture region.

Alternatively, there is the following embodiment.

An immunological detection method, characterized in that the method comprises the following steps:

(1) providing a test sample to a given region between a capture region and one end, closer to a reagent region than the capture region, of a water-absorbent substrate, wherein the capture region immobilized with a first immunochemical component capable of specifically binding to an analyte, and the reagent region maintained in a form capable of releasing by contact with water a labeled component (first labeled component), the first labeled component comprising a second immunochemical component capable of specifically binding to the analyte, a third immunochemical component incapable of binding to the analyte and a labeling substance, wherein the labeling substance is bound to the second and third immunochemical components, are positioned in a given region on a surface thereof;

(2) from said one end of a water-absorbent substrate, developing a mixture comprising:

a solution comprising a labeled component (second labeled component), the second labeled component comprising a fourth immunochemical component capable of specifically binding to the third immunochemical component via a mediating substance, and a labeling substance, wherein the labeling substance is bound to the fourth immunochemical component; and a solution comprising the mediating substance;

(3) binding an immunological complex comprising the analyte, the first labeled component, the mediating substance and the second labeled component to the first immunochemical component immobilized at the capture region, wherein the immunological complex is formed on the water-absorbent substrate, thereby capturing the immunological complex; and (4) thereafter detecting the analyte by determining a signal of the labeling substance on the capture region.

In this Embodiment B-1, the following reactions are carried out in each step. In other words, from one end of the water-absorbent substrate (namely solution-absorbing site), when a mixture comprising:

a solution comprising a test sample, a solution comprising a second labeled component, and a solution comprising a mediating substance for mediating binding of third and fourth immunochemical components (in the mixture, the mediating substance being specifically bound to the fourth immunochemical component in the second labeled component) is added dropwise, and then developed, each component migrates on the water-absorbent substrate along with the migration of the solution. When the solution reaches a reagent region, the first labeled component maintained in the reagent region is released by contact with water from the reagent region. Further, the second immunochemical component in the first labeled component is bound to the analyte in the test sample, and the third immunochemical component is bound to the fourth immunochemical component in the second labeled component via a mediating substance, respectively, thereby further migrating the components on the water-absorbent substrate. Thereafter, the formed immunological complex is bound to the first immunochemical component immobilized at a capture region, thereby capturing the immunological complex on the capture region. As described above, the labeling substance constituting first and second labeled components are assembled and bound at the capture region, so that a detection signal is amplified, whereby the presence of the analyte can be detected at a higher sensitivity.

Another embodiment of the method of the present invention includes a method comprising, instead of adding dropwise a test sample from a solution-absorbing site in the above method, adding dropwise or applying the test sample between the solution-absorbing site and the capture region, and thereafter adding dropwise a mixture comprising:

a solution comprising a second labeled component and a solution comprising a mediating substance to the solution-absorbing site, and thereafter developing the mixture. In this case, when the mixture reaches the region in which a test sample is added dropwise or applied, an analyte in the test sample migrates on the water-absorbent substrate along with the complex of the second labeled component and the mediating substance. When the solution reaches a reagent region, the first labeled component maintained in the reagent region is released by contact with water from the reagent region. Further, the second immunochemical component in the first labeled component is bound to the analyte in the test sample, and the third immunochemical component is bound to the fourth immunochemical component in the second labeled component via a mediating substance, respectively, thereby further migrating the components on the water-absorbent substrate. Thereafter, the formed immunological complex is bound to the first immunochemical component immobilized at a capture region, thereby capturing the immunological complex on the capture region.

2) Embodiment B-2

An immunological detection method, characterized in that the method comprises the following steps:

(1) from one end of a water-absorbent substrate, wherein a capture region immobilized with a first immunochemical component capable of specifically binding to an analyte is positioned in a given region on a surface thereof, developing a mixture comprising:

a solution comprising a labeled component (first labeled component), the first labeled component comprising a second immunochemical component capable of specifically binding to the analyte, a third immunochemical component incapable of binding to the analyte and a labeling substance, wherein the labeling substance is bound to the second and third immunochemical components; and a solution comprising a test sample; and binding an immunological complex of the analyte and the first labeled component to the first immunochemical component immobilized at the capture region, wherein the immunological complex is formed in the mixture, thereby capturing the immunological complex;

(2) thereafter developing on the water-absorbent substrate a solution comprising a mediating substance for mediating binding of the third and fourth immunochemical components, and binding to the third immunochemical component present in the immunological complex captured on the capture region;

(3) further developing on the water-absorbent substrate a solution comprising a labeled component (second labeled component), the second labeled component comprising a fourth immunochemical component capable of specifically binding to the third immunochemical component via a mediating substance, and a labeling substance, wherein the labeling substance is bound to the fourth immunochemical component, and binding to the mediating substance present in the immunological complex captured on the capture region;

(4) thereafter detecting the analyte by determining a signal of the labeling substance on the capture region.

Alternatively, there is the following embodiment.

An immunological detection method, characterized in that the method comprises the following steps:

(1) providing a test sample to a given region between a capture region and one end of a water-absorbent substrate, wherein the capture region immobilized with a first immunochemical component capable of specifically binding to an analyte is positioned in a given region on a surface of the water-absorbent substrate;

(2) from said one end of a water-absorbent substrate, developing a solution comprising a labeled component (first labeled component), the first labeled component comprising a second immunochemical component capable of specifically binding to the analyte, a third immunochemical component incapable of binding to the analyte, and a labeling substance, wherein the labeling substance is bound to the second and third immunochemical components; and binding an immunological complex comprising the analyte and the first labeled component to the first immunochemical component immobilized at the capture region, wherein the immunological complex is formed on the water-absorbent substrate, thereby capturing the immunological complex;

(3) thereafter developing on the water-absorbent substrate a solution comprising a mediating substance for mediating binding of third and fourth immunochemical components, and binding to the third immunochemical component present in the immunological complex captured on the capture region;

(4) further developing on the water-absorbent substrate a solution comprising a labeled component (second labeled component), the second labeled component comprising a fourth immunochemical component capable of specifically binding to the third immunochemical component via a mediating substance, and a labeling substance, wherein the labeling substance is bound to the fourth immunochemical component; and binding to the mediating substance present in the immunological complex captured on the capture region; and (5) thereafter detecting the analyte by determining a signal of the labeling substance on the capture region.

In this Embodiment B-2, the following reactions are carried out in each step. In other words, from one end of the water-absorbent substrate (namely solution-absorbing site), when a mixture comprising:

a solution comprising a test sample and a solution comprising a first labeled component (in the mixture, the analyte and the second immunochemical component in the first labeled component forming a complex) is added dropwise and developed, the resulting immunological complex migrates on the water-absorbent substrate along with the migration of the solution, and is bound to a first immunochemical component immobilized at a capture region, thereby capturing the immunological complex on the capture region. Next, a solution comprising a mediating substance for mediating binding of third and fourth immunochemical components is added dropwise, and developed on the water-absorbent substrate, whereby the mediating substance is bound to the third immunochemical component in the immunological complex captured on the capture region. Further, when a solution comprising a second labeled component is added dropwise, and developed on the water-absorbent substrate, the mediating substance in the immunological complex captured on a capture region is bound to a fourth immunochemical component in the second labeled component, thereby forming a complex of [immobilized first immunochemical component-analyte-first labeled component-mediating substance-second labeled component]. As described above, the labeling substance constituting first and second labeled components is assembled and bound at a capture region, so that the detection signal is amplified, whereby the presence of the analyte can be detected at a higher sensitivity.

In addition, another preferred embodiment includes a method comprising, instead of adding dropwise a test sample from a solution-absorbing site in the above method, adding dropwise or applying the test sample between the solution-absorbing site and the capture region, and thereafter adding dropwise and developing a solution comprising a first labeled component to the solution-absorbing site. In this case, when the solution comprising a first labeled component reaches the region in which a test sample is added dropwise or applied, an analyte in the test sample is bound to a second immunochemical component in the first labeled component, thereby forming an immunological complex. Thereafter, the immunological complex migrates on the water-absorbent substrate along with the migration of the solution, and is bound to the first immunochemical component immobilized on the capture region, thereby capturing the immunological complex.

3) Embodiment B-3

An immunological detection method, characterized in that the method comprises the following steps:

(1) from one end of a water-absorbent substrate, wherein a capture region immobilized with a first immunochemical component capable of specifically binding to an analyte is positioned in a given region on a surface thereof, developing a mixture comprising:

a solution comprising a test sample;

a solution comprising a labeled component (first labeled component), the first labeled component comprising a second immunochemical component capable of specifically binding to the analyte, a third immunochemical component incapable of binding to the analyte and a labeling substance, wherein the labeling substance is bound to the second and third immunochemical components;

a solution comprising a labeled component (second labeled component), the second labeled component comprising a fourth immunochemical component capable of specifically binding to the third immunochemical component via a mediating substance, and a labeling substance, wherein the labeling substance is bound to the fourth immunochemical component; and a solution comprising the mediating substance;

(2) binding an immunological complex comprising the analyte, the first labeled component, the mediating substance and the second labeled component to the first immunochemical component immobilized at the capture region, wherein the immunological complex is formed in the mixture, thereby capturing the immunological complex; and (3) thereafter detecting the analyte by determining a signal of the labeling substance on the capture region.

Alternatively, there is the following embodiment.

An immunological detection method, characterized in that the method comprises the following steps:

(1) providing a test sample to a given region between a capture region and one end of a water-absorbent substrate, wherein the capture region immobilized with a first immunochemical component capable of specifically binding to an analyte is positioned in a given region on a surface thereof;

(2) from said one end of a water-absorbent substrate, developing a mixture comprising:

a solution comprising a labeled component (first labeled component), the first labeled component comprising a second immunochemical component capable of specifically binding to the analyte, a third immunochemical component incapable of binding to the analyte, and a labeling substance, wherein the labeling substance is bound to the second and third immunochemical components;

a solution comprising a labeled component (second labeled component), the second labeled component comprising a fourth immunochemical component capable of specifically binding to the third immunochemical component via a mediating substance, and a labeling substance, wherein the labeling substance is bound to the fourth immunochemical component; and a solution comprising the mediating substance;

(3) binding an immunological complex comprising the analyte, the first labeled component, the mediating substance and the second labeled component to the first immunochemical component immobilized at the capture region, wherein the immunological complex is formed on the water-absorbent substrate, thereby capturing the immunological complex; and (4) thereafter detecting the analyte by determining a signal of the labeling substance on the capture region.

In this Embodiment B-3, the following reactions are carried out in each step. In other words, from one end of the water-absorbent substrate (namely solution-absorbing site), when a mixture comprising:

a solution comprising a test sample, a solution comprising a first labeled component, a solution comprising a second labeled component and a solution comprising a mediating substance for mediating binding of third and fourth immunochemical components (in the mixture, the analyte being bound to the second immunochemical component in the first labeled component, and the third immunochemical component in the first labeled component being bound to the fourth immunochemical component in the second labeled component via the mediating substance, thereby forming an immunological complex of analyte-first labeled component-mediating substance-second labeled component) is added dropwise, and developed, the resulting immunological complex migrates on the water-absorbent substrate along with the migration of the solution, and is bound to a first immunochemical component immobilized to a capture region, thereby capturing the immunological complex on the capture region. As described above, the labeling substance constituting first and second labeled components is assembled and bound at a capture region, and the detection signal is amplified, whereby the presence of the analyte can be detected at a higher sensitivity.

In addition, another one embodiment includes a method comprising, instead of adding dropwise a test sample from a solution-absorbing site in the above method, adding dropwise or applying the test sample between the solution-absorbing site and the capture region, and thereafter adding dropwise a mixture comprising:

a solution comprising a first labeled component, a solution comprising a second labeled component and a solution comprising a mediating substance for mediating binding of third and fourth immunochemical components to the solution-absorbing site, and thereafter developing the mixture. In this case, when the mixture reaches the region in which a test sample is added dropwise or applied, an analyte in the test sample is bound to a second immunochemical component in the complex [first labeled component-mediating substance-second labeled component] formed in the mixed solution. The resulting complex migrates on the water-absorbent substrate along with the migration of the solution, and is bound to the first immunochemical component immobilized on the capture region, thereby capturing the immunological complex.

4) Embodiment B-4

A method characterized in that a reagent region is positioned between a capture region and one end of a water-absorbent substrate, wherein the region is maintained in a form capable of releasing a second labeled component by contact with water, and that the method comprises the following steps:

(1) from said one end of a water-absorbent substrate, developing a mixture comprising:

a solution comprising a test sample;

a solution comprising a first labeled component; and a solution comprising a mediating substance;

(2) binding an immunological complex comprising an analyte, the first labeled component, the mediating substance and the second labeled component to a first immunochemical component immobilized at the capture region, wherein the immunological complex is formed on the water-absorbent substrate, thereby capturing the immunological complex; and (3) thereafter detecting the analyte by determining a signal of a labeling substance on the capture region.

Alternatively, there is the following embodiment.

A method characterized in that a reagent region is positioned between a capture region and one end of a water-absorbent substrate, wherein the region is maintained in a form capable of releasing a second labeled component by contact with water, and that the method comprises the following steps:

(1) providing a test sample to a given region between the capture region and said one end of a water-absorbent substrate;

(2) from said one end of a water-absorbent substrate, developing a mixture comprising:

a solution comprising a first labeled component; and a solution comprising a mediating substance;

(3) binding an immunological complex comprising an analyte, the first labeled component, the mediating substance and the second labeled component to a first immunochemical component immobilized at the capture region, wherein the immunological complex is formed on the water-absorbent substrate, thereby capturing the immunological complex; and (4) thereafter detecting the analyte by determining a signal of a labeling substance on the capture region.

In this Embodiment B-4, the following reactions are carried out in each step. In other words, from one end of the water-absorbent substrate (namely solution-absorbing site), when a mixture comprising:

a solution comprising a test sample, a solution comprising a first labeled component and a solution comprising a mediating substance for mediating binding of third and fourth immunochemical components (in the mixture, the analyte being specifically bound to the second immunochemical component in the first labeled component, and the third immunochemical component in the first labeled component being specifically bound to the mediating substance, thereby forming a complex) is added dropwise, and developed the solution, the resulting complex migrates on the water-absorbent substrate along with the migration of the solution. When the solution reaches the reagent region, the second labeled component maintained in the reagent region is released by contact with water from the reagent region. Further, the fourth immunochemical component in the second labeled component is bound to the third immunochemical component in the first labeled component via the mediating substance, and further migrates on the water-absorbent substrate. Thereafter, the formed immunological complex is bound to the first immunochemical component immobilized to a capture region, thereby capturing the immunological complex on the capture region. As described above, the labeling substance constituting first and second labeled components is assembled and bound at a capture region, and the detection signal is amplified, whereby the presence of the analyte can be detected at a higher sensitivity.

In addition, another embodiment includes a method comprising, instead of adding dropwise a test sample from a solution-absorbing site in the above method, adding dropwise or applying the test sample between the solution-absorbing site and the capture region, and thereafter adding dropwise a mixture comprising:

a solution comprising a first labeled component and a solution comprising a mediating substance to the solution-absorbing site, and thereafter developing the mixture. In this case, when the mixed solution reaches the region in which a test sample is added dropwise or applied, an analyte in the test sample is bound to a complex of the first labeled component and the mediating substance, and migrates on the water-absorbent substrate. When the solution reaches the reagent region, the second labeled component maintained in the reagent region is released by contact with water from the reagent region. Further, the fourth immunochemical component in the second labeled component is bound to the third immunochemical component in the first labeled component via the mediating substance, and further migrates on the water-absorbent substrate. Thereafter, the formed immunological complex is bound to the first immunochemical component immobilized to a capture region, thereby capturing the immunological complex on the capture region.

5) Embodiment B-5

An immunological detection method, characterized in that the method comprises the following steps:

(1) from one end, closer to a reagent region than a capture region, of a water-absorbent substrate, wherein the capture region immobilized with a first immunochemical component capable of specifically binding to an analyte, and the reagent region maintained in a form capable of releasing by contact with water a labeled component (first labeled component) and a labeled component (second labeled component), the first labeled component comprising a second immunochemical component capable of specifically binding to the analyte, a third immunochemical component incapable of binding to the analyte, and a labeling substance, wherein the labeling substance is bound to the second and third immunochemical components; and the second labeled component comprising a fourth immunochemical component capable of specifically binding to the third immunochemical component via a mediating substance, and a labeling substance, wherein the labeling substance is bound to the fourth immunochemical component, are positioned in a given region on a surface thereof, developing a mixture comprising:

a solution comprising a test sample, and a solution comprising the mediating substance;

(2) binding an immunological complex comprising the analyte, the first labeled component, the mediating substance and the second labeled component to the first immunochemical component immobilized at the capture region, wherein the immunological complex is formed on the water-absorbent substrate, thereby capturing the immunological complex; and (3) thereafter detecting the analyte by determining a signal of the labeling substance on the capture region.

Alternatively, there is the following embodiment.

An immunological detection method, characterized in that the method comprises the following steps:

(1) providing a test sample to a given region between a capture region and one end, closer to a reagent region than a capture region, of a water-absorbent substrate, wherein the capture region immobilized with a first immunochemical component capable of specifically binding to an analyte, and the reagent region maintained in a form capable of releasing by contact with water a labeled component (first labeled component) and a labeled component (second labeled component), the first labeled component comprising a second immunochemical component capable of specifically binding to the analyte, a third immunochemical component incapable of binding to the analyte, and a labeling-substance, wherein the labeling substance is bound to the second and third immunochemical components; and the second labeled component comprising a fourth immunochemical component capable of specifically binding to the third immunochemical component via a mediating substance, and a labeling substance, wherein the labeling substance is bound to the fourth immunochemical component, are positioned in a given region on a surface thereof;

(2) from said one end of a water-absorbent substrate, developing a solution comprising the mediating substance;

(3) binding an immunological complex comprising the analyte, the first labeled component, the mediating substance and the second labeled component to the first immunochemical component immobilized at the capture region, wherein the immunological complex is formed on the water-absorbent substrate, thereby capturing the immunological complex; and (4) thereafter detecting the analyte by determining a signal of the labeling substance on the capture region.

In this Embodiment B-5, the following reactions are carried out in each step. In other words, from one end of the water-absorbent substrate (namely solution-absorbing site), when a mixture comprising:

a solution comprising a test sample and a solution comprising a mediating substance for mediating binding of third and fourth immunochemical components is added dropwise, and developed, each component migrates on the water-absorbent substrate along with the migration of the solution. When the solution reaches the reagent region, the first and second labeled components maintained in the reagent region are released by contact with water from the reagent region. Further, the second immunochemical component in the first labeled component is bound to the analyte in the test sample, and the third immunochemical component is bound to the fourth immunochemical component in the second labeled component via the mediating substance, respectively, thereby forming a complex, and further migrates on the water-absorbent substrate. Thereafter, the formed immunological complex is bound to the first immunochemical component immobilized to a capture region, thereby capturing the immunological complex at the capture region. As described above, the labeling substance constituting first and second labeled components is assembled and bound at a capture region, and the detection signal is amplified, whereby the presence of the analyte can be detected at a higher sensitivity.

In addition, another embodiment includes a method comprising, instead of adding dropwise a test sample from a solution-absorbing site in the above method, adding dropwise or applying the test sample between the solution-absorbing site and the capture region, and thereafter adding dropwise a solution comprising a mediating substance to the solution-absorbing site, and then developing the mixture. In this case, when the mixture reaches the region in which a test sample is added dropwise or applied, an analyte in the test sample migrates on the water-absorbent substrate along with the mediating substance. When the solution reaches the reagent region, the first and second labeled components maintained in the reagent region are released by contact with water from the reagent region. Further, the second immunochemical component in the first labeled component is bound to the analyte in the test sample, and the third immunochemical component is bound to the fourth immunochemical component in the second labeled component via the mediating substance, respectively, thereby forming a complex, and the complex further migrates on the water-absorbent substrate. Thereafter, the formed immunological complex is bound to the first immunochemical component immobilized to a capture region, thereby capturing the immunological complex on the capture region.

In any of these Embodiments B-1 to B-5, a separation region capable of separating an analyte from other substances contained in a test sample may be further positioned in a given region between a capture region and said one end of a water-absorbent substrate, with the proviso that in a case where the test sample is provided to a given region between the capture region and said one end of a water-absorbent substrate, the separation region is positioned from the above region, inclusive, to the capture region.

In addition, in Embodiments B-1, B-4 and B-5, a water-absorbent substrate may be a substrate in which a separation region capable of separating an analyte from other substances contained in a test sample is further positioned in a given region between a capture region and one end closer to a reagent region than the capture region, with the proviso that in a case where the test sample is provided to a given region between the capture region and said one end of a water-absorbent substrate, the separation region is positioned from the above region, inclusive, to the capture region. In this case, the separation region is positioned, for instance, in a given region between one end of the water-absorbent substrate and the reagent region.

The analyte which can be detected by the method of this Embodiment B may be the same as those of Embodiment A. The first immunochemical component and the second immunochemical component may be the same as those of Embodiment A. When both of the first and second immunochemical components are antibodies, a first antibody and a second antibody may be identical ones or different ones. In addition, as different antibodies, there can be used two kinds of antibodies recognizing an identical antigenic determinant, or two kinds of antibodies each recognizing different antigenic determinants.

In the present invention, the third immunochemical component used as the first labeled component and the fourth immunochemical component used as the second labeled component are antibodies (which may be a monoclonal antibody or a polyclonal antibody, or alternatively may be fragmented antibodies such as H chain, L chain, Fab, F(ab')$_2$, V$_H$ and V$_L$) or antigens (for instance, proteins, peptides, haptenes and the like), the antibodies and antigens of which are capable of specifically binding to each other via a mediating substance, wherein the third and fourth immunochemical components do not possess specific affinity with an analyte and an immobilized first immunochemical component. Preferably, these immunochemical components are components which do not further have specific affinity to the second immunochemical component.

The mediating substance in the present invention for mediating binding of the third and fourth immunochemical components is not particularly limited, as long as the mediating substance is a substance capable of forming a complex of [third immunochemical component-mediating substance-fourth immunochemical component] by binding simultaneously to the third and fourth immunochemical components. Preferably, the mediating substance is an immunochemical component capable of specifically binding to the third and fourth immunochemical components via an antigen-antibody reaction. In other words, if the third immunochemical component is an antibody, it is preferable that the mediating substance is an antigen recognized by the antibody, or a secondary antibody capable of specifically binding to the antibody, and that the fourth immunochemical component is an antibody capable of specifically binding to the antigen, or an antigen recognized by the secondary antibody. In this case, when both of the third and fourth immunochemical components are antibodies, these may be identical antibodies or different ones. On the other hand, when the third immunochemical component is an antigen, the mediating substance is an antibody capable of specifically binding to the antigen, and the fourth immunochemical component is an antigen recognized by the antibody or a secondary antibody capable of specifically binding to the antibody. When both of the third and fourth immunochemical components are antigens, these may be identical antigens, or different antigens having cross-reactivities with an antibody, which is a mediating substance. As the third and fourth immunochemical components and the mediating substance, there can be appropriately selected those of known ones used in sandwich method or the like to be used.

The water-absorbent substrate and the capture region usable for the method of this Embodiment B may be the same as those of Embodiment A. In addition, the site at which absorption of the solution comprising a test sample, the solution comprising a first labeled component, the solution comprising a second labeled component, the solution comprising a mediating substance, and the like is initiated (namely, a solution-absorbing site) may be the same as those of Embodiment A. The solution-absorbing site is not particularly limited, as long as it does not prevent solutions each comprising a test sample, labeled components and a mediating substance from migrating to on a water-absorbent substrate.

In addition, the first labeled component in the method of this Embodiment B is a component which comprises an immunochemical component (second immunochemical component) capable of specifically binding to an analyte, a third immunochemical component incapable of binding to the analyte, and a labeling substance, wherein the labeling substance is bound to the second immunochemical component and the third immunochemical component. Also, the second labeled component is a component which comprises an immunochemical component (fourth immunochemical component) capable of specifically binding to the third immunochemical component via a mediating substance, and a labeling substance, wherein the labeling substance is bound to the fourth immunochemical component. The labeling substances usable herein may be the same as those of Embodiment A, and it is preferable that the labeling substance usable for the first and second labeled components is identical.

The method for labeling both of the second and third immunochemical components and the fourth immunochemical component by colored particles may also be the same as those of Embodiment A.

The solution comprising a first labeled component, the solution comprising a second labeled component, and the solution comprising a mediating substance are prepared by dispersing (dissolving) each of the labeled components or the mediating substance in an appropriate dispersion medium (solvent). The dispersion medium for dispersing each of the labeled components or the mediating substance is not particularly limited, as long as it does not inhibit specific binding reactions between an analyte and a first labeled component, between the first labeled component and a mediating substance, and between the mediating substance and a second labeled component. Preferably, a buffer having appropriate pH and salt concentration for the antigen-antibody reaction, including, for instance, phosphate buffer, acetate buffer, borate buffer, Tris-HCl buffer or the like can be appropriately selected to be used. The concentration of each labeled component during the signal detection is in the range of from 0.005 to 5%, preferably from 0.01 to 0.5%. When the concentration is too low, the number of particles bound to the capture region is small, so that the detection sensitivity becomes poor. In addition, when the concentration is too high, it is not only economically disadvantageous but also there arise problems that excessive labeling substances remain on parts other than the capture region, thereby making the signal in the capture region unclear.

In the method of this Embodiment B, the reagent region means a region positioned between the solution-absorbing site and the capture region of the water-absorbent substrate, wherein the region is maintained in a form capable of releasing by contact with water the first labeled component and/or the second labeled component. When both of the first and second labeled components are maintained, a first reagent region maintaining a first labeled component and a second reagent region maintaining a second labeled component may be prepared separately, or the first and second labeled components are mixed to be maintained in one reagent region.

The method for preparing a reagent region is not particularly limited, and there can be included, for instance, a method comprising applying a solution comprising a labeled component to a given region between a solution-absorbing site and a capture region of the water-absorbent substrate, and drying under appropriate conditions (for instance, lyophilization). Alternatively, a labeled component is dispersed in a water-soluble polymer or a saccharose solution, and the dispersed solution is applied onto a water-absorbent substrate, and dried in the same manner. In this method, the water-soluble polymer or saccharose is easily dissolved in water, and the labeled component is quickly released from the substrate, so that the labeled component is capable of reacting with the other labeled component via an analyte in a test sample and/or a mediating substance, and at the same time an appropriate viscosity for maintaining a labeled component in a given region of the water-absorbent substrate can be obtained by adjusting the concentration of a water-soluble polymer or saccharose, thereby making it further advantageous in the aspects that the agglomeration and denaturation of the labeled component can be prevented during drying, and that the labeled component after drying is less likely to be released from the water-absorbent substrate.

As the water-soluble polymer, there are preferably used, for instance, polyvinyl pyrrolidones, polyvinyl alcohols, polyethylene glycols, cellulose esters (for instance, methyl cellulose, ethyl cellulose, carboxymethyl cellulose, carboxyethyl cellulose, hydroxyethyl cellulose, cyan ethyl cellulose, and the like), gelatins, and the like.

The kit for immunochemical detection of the present invention usable for Embodiment B can be preferably used in the immunological detection method of the present invention. The kit comprises a water-absorbent substrate in which a capture region immobilized with a first immunochemical component capable of specifically binding to an analyte is positioned in a given region on a surface thereof; a labeled component (first labeled component), the first labeled component comprising a second immunochemical component capable of specifically binding to the analyte, a third immunochemical component incapable of binding to the analyte, and a labeling substance, wherein the labeling substance is bound to the second and third immunochemical components; a labeled component (second labeled component), the second labeled component comprising a fourth immunochemical component capable of specifically binding to the third immunochemical component via a mediating substance, and a labeling substance, wherein the labeling substance is bound to the fourth immunochemical component; and a mediating substance for mediating binding of the third and fourth immunochemical components.

The preferred embodiments for the water-absorbent substrate, the first and second labeled components and the mediating substance are those preferably used in the method of the present invention as described above.

In one preferred embodiment of the water-absorbent substrate usable for the kit of the present invention, a reagent region maintained in a form capable of releasing by contact with water at least one of first and second labeled components may be further positioned between a capture region and said one end of a water-absorbent substrate.

In addition, one preferred embodiment of the water-absorbent substrate usable for the kit of the present invention includes a substance in which a separation region capable of separating an analyte from other substances contained in a test sample is further positioned in a given region between a capture region and said one end of a water-absorbent substrate, with the proviso that in a case where the test sample is added dropwise or applied to a given region between the capture region and said one end of a water-absorbent substrate, the separation region is positioned from the above region, inclusive, to the capture region.

Another preferred embodiment of the water-absorbent substrate usable for the kit of the present invention includes a substrate in which a separation region capable of separating an analyte from other substances contained in a test sample is further positioned in a given region between a capture region and one end closer to a reagent region than the capture region, with the proviso that in a case where the test sample is provided to a given region between the capture region and said one end of a water-absorbent substrate, the separation region is positioned from the above region, inclusive, to the capture region. In this case, the separation region is positioned in a given region between the reagent region and one end of the water-absorbent substrate.

In the present invention, it is desired that the separation region has a pore size in a direction to be separated larger than the sizes of an analyte, each labeled component and a mediating substance, and smaller than other substances in a test sample to be separated and removed. In addition, the direction of separation may be a direction of developing a labeled component on a water-absorbent substrate, or a direction perpendicular to the above direction. Further, after the analyte is separated from other substances in the test sample, the separation region may be removed and then the subsequent assay may be carried out.

The materials for the separation region include, for instance, nonwoven fabrics such as rayon and polyesters, filter paper, glass fiber cloth, glass filter, nitrocellulose filter, polysulfone filter, porous materials, and the like.

The kit of the present invention may comprise additional ingredients which can be preferably used in the immunological detection method of the present invention in addition to the ingredients described above. For instance, there are cited the above buffers preferably usable for dispersing the first and second labeled components and the mediating substance.

[3] Embodiment C

Embodiment C is a sandwiched-type immunological detection method wherein at a capture region immobilized with a first immunochemical component capable of binding to an analyte, the analyte is sandwiched by the first immunochemical component and a labeled component comprising a second immunochemical component capable of binding to the analyte and a labeling substance, wherein the labeling substance is bound to the second immunochemical component, characterized in that the immunological detection method comprises forming a complex via binding between a biotin and an avidin, and detecting the analyte.

When this embodiment is carried out, there are the following three embodiments.

(1) Embodiment C-1

The immunological detection method, characterized in that the method comprises forming a complex of the labeling substance via an avidin capable of binding to the biotin, wherein the labeling substance is further bound to a biotin [for instance, water-absorbent substrate-first immunochemical component-analyte-second immunochemical component-labeling substance-biotin-avidin-biotin-labeling substance-second immunochemical substance], thereby detecting the analyte by the labeling substance in the complex.

In this case, there may be used an avidin which is maintained in a form capable of releasing by contact with water in a given region between the capture region and one end of the water-absorbent substrate.

(2) Embodiment C-2

The immunological detection method, characterized in that the method comprises using as the labeled component a conjugate comprising the second immunochemical component, a first labeling substance and an avidin, and then reacting the conjugate together with a conjugate comprising a biotin and a second labeling substance, thereby forming a complex via binding between the avidin and the biotin [for instance, water-absorbent substrate-first immunochemical component-analyte-second immunochemical component-first labeling substance-avidin-biotin-second labeling substance]; and detecting the analyte by the first and second labeling substances in the complex.

In this case, there may be used the conjugate comprising a biotin and the second labeling substance which is maintained in a form capable of releasing by contact with water in a given region between the capture region and one end of the water-absorbent substrate.

(3) Embodiment C-3

The immunological detection method, characterized in that the method comprises using as the labeled component a conjugate comprising the second immunochemical component, a first labeling substance and a biotin, and then reacting the conjugate with a conjugate comprising an avidin and a second labeling substance, thereby forming a complex via binding between the biotin and the avidin [for instance, water-absorbent substrate-first immunochemical component-analyte-second immunochemical component-first labeling substance-biotin-avidin-second labeling substance]; and detecting the analyte by the first and second labeling substances in the complex.

In this case, there may be used the conjugate comprising an avidin and the second labeling substance which is maintained in a form capable of releasing by contact with water in a given region between the capture region and one end of the water-absorbent substrate.

The analyte referred to in this embodiment is the same as the analyte described in Embodiment A.

The first immunochemical component and the second immunochemical component each capable of binding to the analyte mentioned above are the same ones as the first immunochemical component and the second immunochemical component as described in Embodiment A, each of which is capable of specifically binding to an analyte to be detected, which include antibodies or antigens (here, antigens include proteins, peptides, haptene, and the like), wherein those known to be usable for sandwich method or the like, depending upon analytes to be detected are appropriately selected. For instance, when the analyte is an antigen, a corresponding antibody can be used as an immunochemical component. In this case, as the first immunochemical component immobilized to a capture region and the second immunochemical component used as a constituent for a labeled component, there can be used a polyclonal antibody or a monoclonal antibody. When one of the immunochemical components is a monoclonal antibody, it is preferable that the other immunochemical component is one recognizing an antigenic determinant different from that recognized by the monoclonal antibody. On the other hand, when an analyte is an antibody, a corresponding antigen can be used as an immunochemical component. In this case, as the first immunochemical component and the second immunochemical component, there can be used a corresponding antigen and an anti-antibody (anti-immunoglobulin antibody) against an antibody, which is the analyte, respectively.

The water-absorbent substrate in the present invention is the same one as in the water-absorbent substrate described in Embodiment A, and it is not particularly limited, as long as it can absorb a test sample comprising an analyte including, for instance, serum, blood, urea, feces, saliva, or the like, or it can absorb a dilution prepared by diluting the test sample mentioned above with a buffer, and it can absorb a solution comprising a labeled component. The buffer used herein is not particularly limited, and includes borate buffer, phosphate buffer, Tris-HCl buffer, and the like.

The capture region in the present invention refers to a region in which the first immunochemical component mentioned above is immobilized on the water-absorbent substrate mentioned above. A method for immobilizing a first immunochemical component on a water-absorbent substrate (a method for preparing a capture region) is not particularly limited, and those immobilized by conventionally known physical adsorption method and covalent bonding method are preferable.

The amount of the first immunochemical component immobilized differs depending upon the immunochemical components used and properties thereof, and the amount is usually about 0.001 to about 10 mg/cm$^2$.

In addition, it is preferable that the water-absorbent substrate after formation of the capture region is blocked with a surfactant, or with a protein or with a water-soluble polymer in order to prevent non-specific adsorption of an analyte or a labeled component, wherein the surfactant includes polyoxyethylene(20) sorbitan monolaurate (Tween™ 20), polyoxyethylene(20) sorbitan monooleate (Tween™ 80), polyoxyethylene(10) octylphenyl ether (Triton™ X-100), sodium dodecylbenzensulfonate, and the like; the protein includes bovine serum albumin, skim milk, casein, and the like; and the water-soluble polymer includes polyethylene glycols, polyvinyl alcohols, polyvinyl pyrrolidones, and the like.

The labeled component in the present invention as referred to in Embodiment C-1 is a conjugate comprising a labeling substance, the second immunochemical component, and further a biotin, wherein the labeling substance is bound to the second immunochemical component, wherein the substance is further bound to a biotin; the labeled component as referred to in Embodiment C-2 is a conjugate comprising the second immunochemical component, a first labeling substance and an avidin; and the labeled component as referred to in Embodiment C-3 is a conjugate comprising the second immunochemical component, a first labeling substance and a biotin. The labeling substance or the first labeling substance used herein is not particularly limited, and the colored particles are preferable from the viewpoint of simplicity in detection. The colored particles are not limited, as long as their coloring is visually detectable, and are the same as the colored particles described in Embodiment A.

The biotin is not particularly limited, as long as it is capable of specifically binding to the avidin, which may be biotin or derivatives thereof. The biotin derivatives include, for instance, methyl ester of biotin, biotinol, biotinyl ω-bromide, biocytin, desthiobiotin, biotin L-sulfoxide, and the like. In particular, biotin and biocytin are preferable.

The avidin is not particularly limited, as long as it is capable of specifically binding to the biotin. The avidin may be those isolated from egg white, or it may be streptoavidin isolated from *Streptomyces avidinii*. In particular, avidin is preferable.

As a method for binding the second immunochemical component and a biotin to the colored particles or a method for binding the second immunochemical component and an avidin to the colored particles, there can be employed conventionally well known methods, including covalent bonding method, physical adsorption method, ionic bonding method, and the like. From the aspect that the second immunochemical component and a biotin after binding to the colored particles, or the second immunochemical component and an avidin after binding to the colored particles, are not released therefrom and thus being stable, it is preferable to employ the covalent bonding method. Although the color of the colored particles to which the second immunochemical component and a biotin are bound, or to which the second immunochemical component and an avidin are bound may be different, it is preferable that the colored particles are identical to each other.

The labeled components obtained in the manner described above can be used by dispersing in a buffer. The buffer used herein includes borate buffer, phosphate buffer, Tris-HCl buffer, and the like, and there is appropriately used a buffer having pH and a salt concentration so as not to inhibit an antigen-antibody reaction. The amount of the labeled component used can be appropriately set in each of the embodiments of the present invention. For instance, the concentration of the labeled component in a buffer containing the labeled component is in ranges of from 0.005 to 5% by weight, preferably from 0.01 to 0.5% by weight. When the concentration is too low, the number of the colored particles bound to a captured region is small, thereby making the coloring poor. In addition, when the concentration is too high, there arise such problems that not only it is economically disadvantageous, but also excessive colored particles remain on parts other than the capture region, thereby making the coloring of the capture region unclear (hereinafter, a buffer comprising labeled components is also referred to as a labeled component solution).

The conjugate comprising a biotin and the second labeling substance usable for the method (Embodiment C-2) of the present invention is a conjugate comprising a labeling substance and a biotin, wherein a biotin is bound to the labeling substance, in which the labeling substance may be the same ones as those in the first labeling substance. Although the colors of the colored particles preferably usable for the first labeling substance and the second labeling substance may be different, it is preferable that the colored particles are identical to each other. Similarly, the conjugate comprising an avidin and the second labeling substance usable for the method (Embodiment C-3) of the present invention is a conjugate comprising a labeling substance and an avidin, wherein an avidin is bound to the labeling substance, in which the labeling substance may be the same ones as those in the first labeling substance. Although the colors of the colored particles preferably usable for the first labeling substance and the second labeling substance may be different, it is preferable that the colored particles are identical to each other.

As a method for binding a biotin or an avidin to the colored particles, there can be employed conventionally well known methods, including covalent bonding method, physical adsorption method, ionic bonding method, and the like. From the aspect that a biotin or an avidin after binding to the colored particles is not released therefrom and thus being stable, it is preferable to employ the covalent bonding method.

As a method of applying an avidin in Embodiment C-1, a method of applying a conjugate comprising a biotin and a second labeled substance in Embodiment C-2, or a method of applying a conjugate comprising an avidin and a second labeled substance in Embodiment, it may be maintained in a form capable of releasing by contact with water in a given region between one end of the water-absorbent substrate and the capture region in which the first immunochemical component is immobilized, or it may be used by mixing with a labeled component solution. In addition, it may be used by mixing with a buffer. The buffer used herein includes the same ones usable for dispersing the labeled component.

In the present invention, it is preferable to apply on the water-absorbent substrate such that in Embodiment C-1 an avidin is capable of being released from the water-absorbent substrate by contact with water such as a test sample, a buffer, or the like, that in Embodiment C-2 a conjugate comprising a biotin and a second labeling substance is capable of being released from the water-absorbent substrate by contact with water such as a test sample, a buffer, or the like, or that in Embodiment C-3 a conjugate comprising an avidin and a second labeling substance is capable of being released from the water-absorbent substrate by contact with water such as a test sample, a buffer, or the like. An application method includes, for instance, a process comprising applying on a water-absorbent substrate a solution of an avidin in Embodiment C-1, a solution of a conjugate comprising a biotin and a second labeling substance in Embodiment C-2, or a solution of a conjugate comprising an avidin and a second labeling substance in Embodiment C-3; and thereafter drying under appropriate conditions. As one embodiment of drying, lyophilization can be employed. Also, a labeling substance is dispersed in a water-soluble polymer or a saccharose solution, and the dispersion is applied on a water-absorbent substrate, and the resulting substrate is similarly dried. In this method, the water-soluble polymer or saccharose is readily solubilized, so that the labeling substance is quickly released from the substance to, thereby allowing to react with the other labeling substance via an analyte in a test sample and/or a mediating substance. At the same time, by adjusting the concentration of the water-soluble polymer or saccharose, there are such an advantage that a viscosity appropriate for maintaining the labeling substance in a given region of the water-absorbent substrate can be obtained, that agglomeration and denaturation of the labeling substance are prevented during drying, or that the labeling substance is less likely to be released from the water-absorbent substrate after drying.

Since the sandwiched-type immunoassay of the present invention has a high affinity between the avidin and the biotin, such that a plurality of biotins are capable of binding to one molecule of an avidin, in Embodiment C-1, a further higher order complex is formed by binding a large number of biotin-bound labeled components via an avidin to a complex of an analyte with a first immunochemical component in a capture region. Consequently, there is exhibited an effect that a binding signal of the analyte and the first immunochemical component is amplified, so that the detection of the colored labeled component is made easy. Similarly in Embodiments C-2 and C-3, when a complex of an analyte with a first immunochemical complex in a capture region is bound to a labeled component, a further higher order complex is formed via a conjugate comprising a biotin and a second labeling substance or a conjugate comprising an avidin and a second labeling substance. Consequently, there is exhibited an effect that a binding signal of an analyte with a first immunochemical component is amplified, so that a visual detection is made easy by the colored labeled components and the second labeling substance.

In other words, the complex in the present invention for Embodiment C-1 can be expressed in the simplest binding form as water-absorbent substrate-first immunochemical component-analyte-second immunochemical component-labeling substance-biotin-avidin-biotin-labeling substance-second immunochemical component. Since a plural number of the -biotin-labeling substance-second immunochemical component bound to an avidin can be bound to the same avidin molecule, it can be expressed as water-absorbent substrate-first immunochemical component-analyte-second immunochemical component-labeling substance-biotin-avidin-(biotin-labeling substance-second immunochemical component)n.

In addition, since an analyte is further bindable to a second immunochemical component positioned at the end of the complex, the analyte is further bound to the second immunochemical component, whereby subsequently there can be also bound the -second immunochemical component-labeling substance-biotin-avidin-(biotin-labeling substance-second immunochemical component)n. In other words, there is formed a complicated complex having a structure: water-absorbent substrate-first immunochemical component-analyte-second immunochemical component-labeling substance-biotin-avidin-(biotin-labeling substance-second immunochemical component)n-[analyte-second immunochemical component-labeling substance-biotin-avidin-(biotin-labeling substance-second immunochemical component)n]n-.

These complexes in the present invention are one example, and various complicated complexes via biotin-avidin binding are included.

In addition, in Embodiment C-2, it can be expressed in the simplest binding form as water-absorbent substrate-first immunochemical component-analyte-second immunochemical component-first labeling substance-avidin-biotin-second labeling substance. Since a plural number of the -biotin-second labeling substance bound to an avidin can be bound to the same avidin molecule, it can be expressed, for instance, as water-absorbent substrate-first immunochemical component-analyte-second immunochemical component-first labeling substance-avidin-(biotin-second labeling substance)n.

The second labeling substance positioned at the end of the complex mentioned above is bound to a large number of biotins, and each of the biotins is further bound to an avidin bound to a different first labeling substance, thereby forming various complicated complexes via biotin-avidin binding.

In addition, in Embodiment C-3, it can be expressed in the simplest binding form as water-absorbent substrate-first immunochemical component-analyte-second immunochemical component-first labeling substance-biotin-avidin-second labeling substance. In addition, since a plural number of the biotin-first labeling substance-second immunochemical component bound to an avidin can be bound to the same avidin molecule, and the first labeling substance is further bound to a large number of biotins, and each of biotins is further bound to an avidin bound to a different second labeling substance, thereby forming various complicated complexes via biotin-avidin binding.

In the present invention, the distance between the above capture region and the site at which absorption of solutions of a test sample, a labeled component solution, or a mixture comprising a test sample and a labeled component solution; a buffer, or the like is initiated (hereinafter also referred to as dropping site) is from 1 to 6 cm, preferably from 2 to 4 cm or so. When the distance is too far, there are undesirably likely to cause such problems that the analyte and the labeled component do not reach to the capture region, that the sensitivity of the coloring becomes too intensive, or that a long period of time is necessary for assaying. On the other hand, when the distance is too close, there are undesirably likely to cause such problems that the coloring in the capture region is not uniform but becomes uneven, or that the sensitivity of the detection signal becomes too low.

Embodiments for the immunological detection method of the present invention will be explained below.

Figure 10:
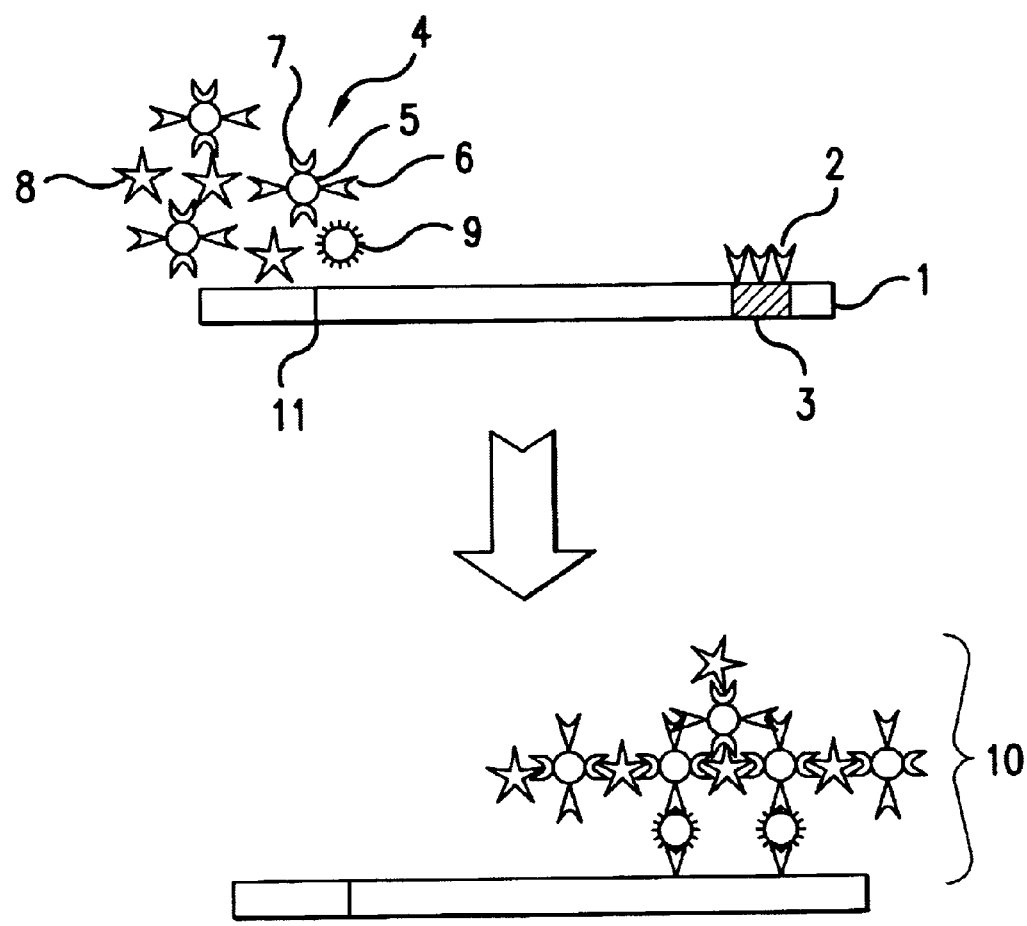
FIG. 10 is a schematic view showing one embodiment of the immunological detection method of the present invention (Embodiment C-1).

In Embodiment C-1, there are exemplified the following two embodiments. In a first embodiment, as shown in FIG. 10, a test sample is mixed with a buffer comprising a labeled component 4, and an avidin 8, and the resulting mixture is developed from a dropping site 11 on a water-absorbent substrate 1, thereby allowing the mixture to migrate to a capture region 3 to which a first immunochemical component 2 is immobilized. During this period, a binding of a second immunochemical component 6 in the labeled component 4 with an analyte 9, and a binding of a biotin 7 and an avidin 8 in the labeled component 4 take place. When the mixture reaches the capture region 3, the first immunochemical component 2 immobilized on the water-absorbent substrate 1 is bound to the analyte 9, thereby forming a complex 10 [water-absorbent substrate-first immunochemical component-analyte-second immunochemical component-labeling substance-biotin-avidin-labeling substance].

Figure 11:
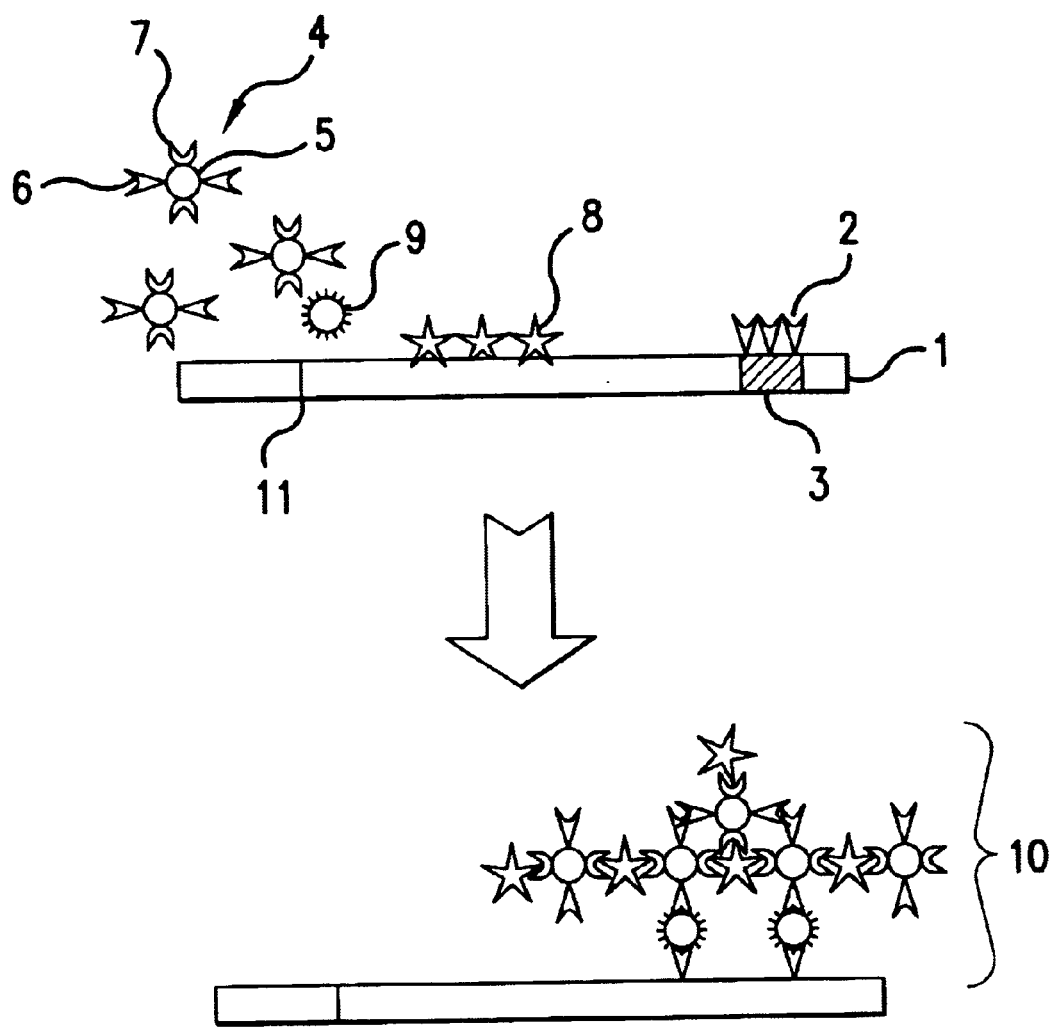
FIG. 11 is a schematic view showing another embodiment of the immunological detection method of the present invention (Embodiment C-1).

In a second embodiment, as shown in FIG. 11, from a dropping site 11 on a water-absorbent substrate 1, a test sample is developed along with a buffer comprising a labeled component 4, thereby allowing the mixture to migrate to a capture region 3 to which a first immunochemical component 2 is immobilized. In a part way of the migration, the mixture reaches a region to which an avidin 8 is applied (avidin region), and the avidin 8 is released by contact with water. Further, during the period in which the solution migrates on the water-absorbent substrate 1 to reach the capture region 3 in which a first immunochemical component 2 is immobilized, a binding of a second immunochemical component 6 in the labeled component 4 with an analyte 9 in the test sample, and a binding of a biotin 7 in the labeled component 4 and an avidin 8, wherein the avidin is immobilized on the water-absorbent substrate 1 but released therefrom by contact with water, take place. When the mixture reaches the capture region 3, the first immunochemical component 2 immobilized on the water-absorbent substrate is bound to the analyte 9, thereby forming a complex 10 [water-absorbent substrate-first immunochemical component-analyte-second immunochemical component-labeling substance-biotin-avidin-labeling substrate].

The complex 10 formed as described above can be visually confirmed, since the colored particles as a labeling substance 5 constituting an immunolabeled component are assembled by higher order binding via avidin-biotin, so that the coloring is clear.

Figure 12:
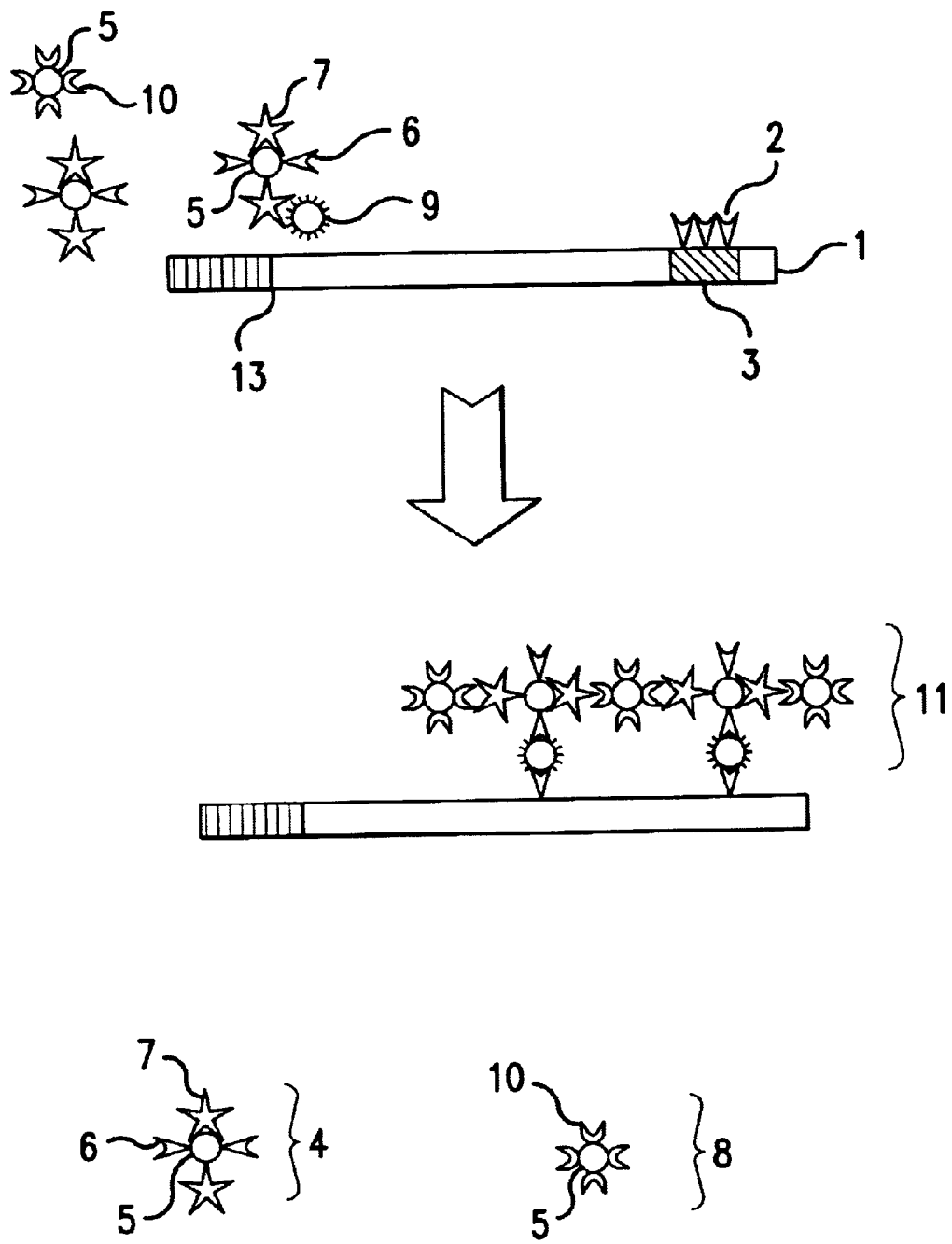
FIG. 12 is a schematic view showing one embodiment of the immunological detection method of the present invention (Embodiment C-2).

In Embodiment C-2, there are exemplified the following two embodiments. In a first embodiment, as shown in FIG. 12, a test sample is mixed with a buffer containing a labeled component 4, and a conjugate 8 comprising a biotin and a second labeling substance, and the resulting mixture is developed from a dropping site 13 on a water-absorbent substrate 1, thereby allowing the mixture to migrate to a capture region 3 to which a first immunochemical component 2 is immobilized. During this period, a binding of a second immunochemical component 6 in the labeled component 4 with an analyte 9, and a binding of an avidin 7 in the labeled component 4 with a biotin 10 in the conjugate 8 comprising a biotin and the second labeling substance take place. When the mixture reaches the capture region 3, the first immunochemical component 2 immobilized on the water-absorbent substrate 1 is bound to the analyte 9, thereby forming a complex 11 [water-absorbent substrate-first immunochemical component-analyte-second immunochemical component-first labeling substance-avidin-biotin-second labeling substrate].

Figure 13:
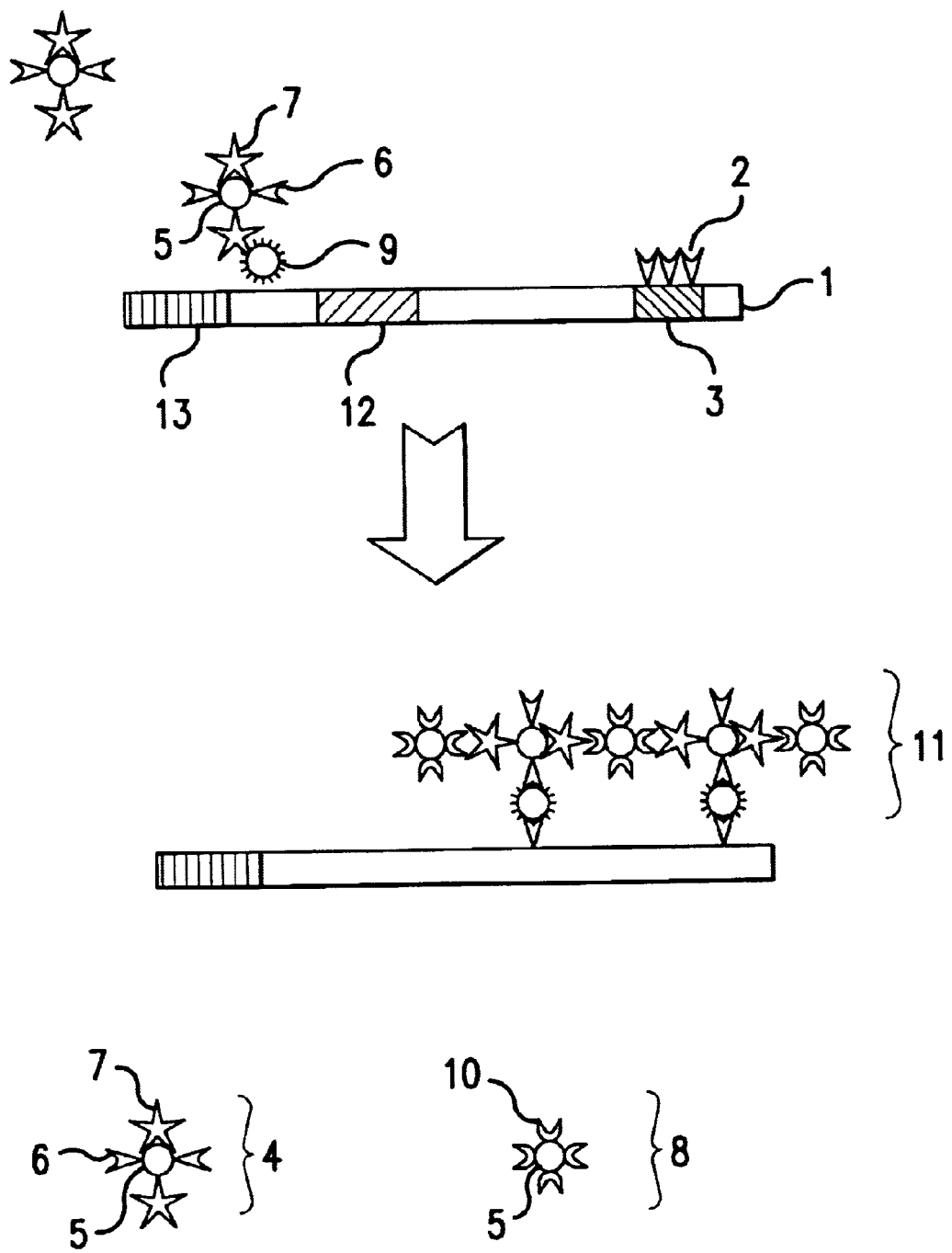
FIG. 13 is a schematic view showing another embodiment of the immunological detection method of the present invention (Embodiment C-2).

In a second embodiment, as shown in FIG. 13, from a dropping site 13 on a water-absorbent substrate 1, a test sample is developed along with a buffer containing a labeled component 4, thereby allowing the mixture to migrate to a capture region 3 to which a first immunochemical component 2 is immobilized. In a part way of the migration, the mixture reaches a reagent region 12 to which the conjugate 8 comprising a biotin and a second labeling substance is applied, and the conjugate 8 comprising a biotin and the second labeling substance is released by contact with water. Further, during the period in which the mixture migrates on the water-absorbent substrate 1 to reach the capture region 3 in which a first immunochemical component 2 is immobilized, a binding of a second immunochemical component 6 in the labeled component 4 with an analyte 9 in the test sample, and a binding of an avidin 7 in the labeled component 4 with a biotin 10 contained in the conjugate 8 comprising a biotin and the second labeling substance, wherein the biotin is immobilized on the water-absorbent substrate 1 but released therefrom by contact with water, take place. When the solution reaches the capture region 3, the first immunochemical component 2 immobilized on the water-absorbent substrate is bound to the analyte 9, thereby forming a complex 11 [water-absorbent substrate-first immunochemical component-analyte-second immunochemical component-first labeling substance-avidin-biotin-second labeling substance].

The complex 11 formed as described above can be visually confirmed, since the colored particles as a first labeling substance 5 and a second labeling substance 5 are assembled by higher order binding via avidin-biotin, so that the coloring is clear.

Figure 14:
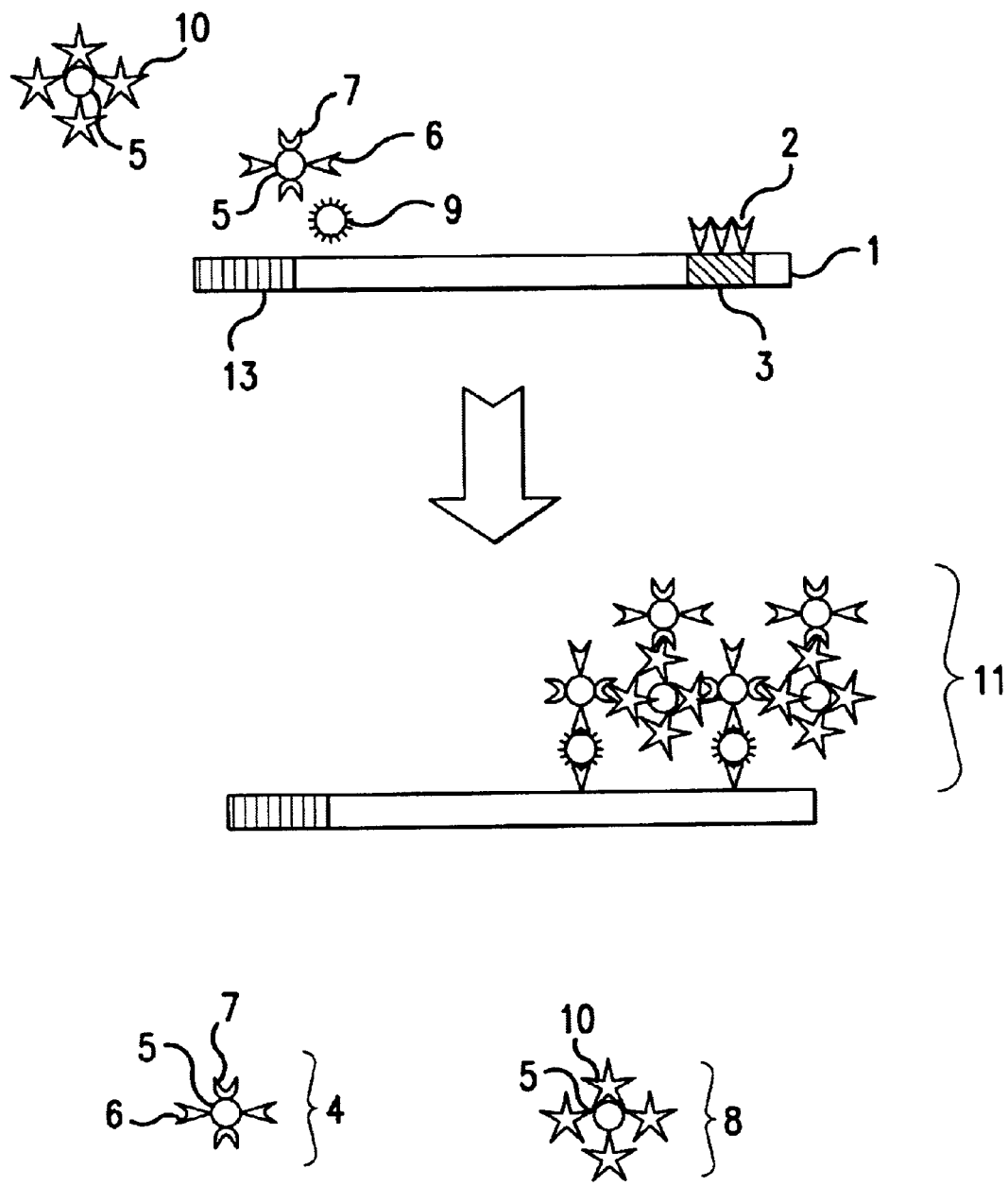
FIG. 14 is a schematic view showing one embodiment of the immunological detection method of the present invention (Embodiment C-3).

In Embodiment C-3, there are exemplified the following two embodiments. In a first embodiment, as shown in FIG. 14, a test sample is mixed with a buffer comprising a labeled component 4, and a conjugate 8 comprising an avidin and a second labeling substance, and the resulting mixture is developed from a dropping site 13 on a water-absorbent substrate 1, thereby allowing the mixture to migrate to a capture region 3 to which a first immunochemical component 2 is immobilized. During this period, a binding of a second immunochemical component 6 in the labeled component 4 with an analyte 9, and a binding of a biotin 7 in the labeled component 4 with an avidin 10 in the conjugate 8 comprising an avidin and the second labeling substance take place. When the mixture reaches the capture region 3, the first immunochemical component 2 immobilized on the water-absorbent substrate 1 is bound to the analyte 9, thereby forming a complex 11 [water-absorbent substrate-first immunochemical component-analyte-second immunochemical component-first labeling substance-biotin-avidin-second labeling substance].

Figure 15:
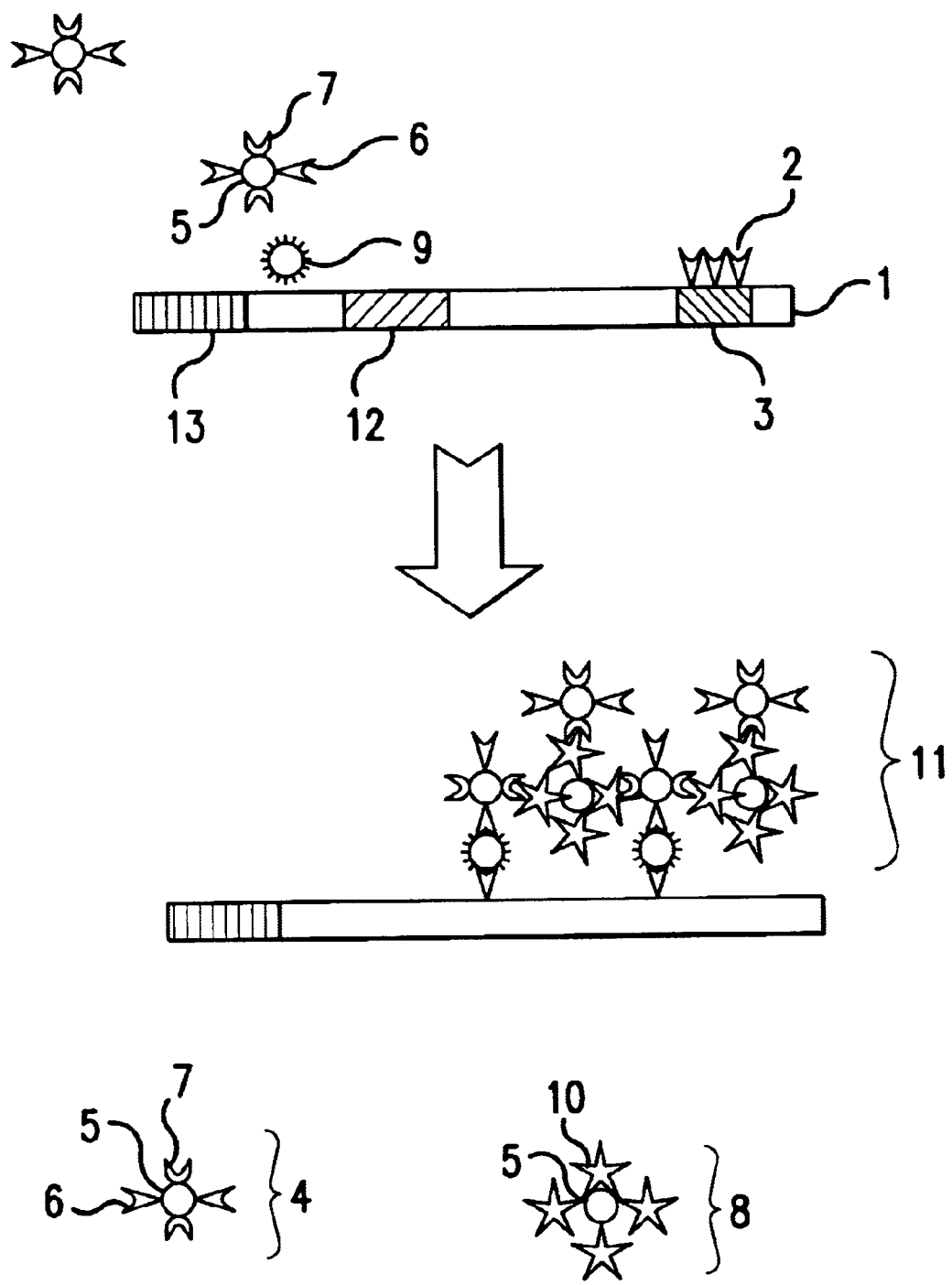
FIG. 15 is a schematic view showing another embodiment of the immunological detection method of the present invention (Embodiment C-3).

In a second embodiment, as shown in FIG. 15, from a dropping site 13 on a water-absorbent substrate 1, a test sample is developed along with a buffer comprising a labeled component 4, thereby allowing the mixture to migrate to a capture region 3 to which a first immunochemical component 2 is immobilized. In a part way of the migration, the mixture reaches a reagent region 12 to which the conjugate 8 comprising an avidin and a second labeling substance is applied, and the conjugate 8 comprising an avidin and the second labeling substance is released by contact with water. Further, during the period in which the solution migrates on the water-absorbent substrate 1 to reach the capture region 3 in which a first immunochemical component 2 is immobilized, a binding of a second immunochemical component 6 in the labeled component 4 with an analyte 9 in the test sample, and a binding of a biotin 7 in the labeled component 4 with an avidin 10 contained in the conjugate 8 comprising an avidin and the second labeling substance, wherein the avidin is immobilized on the water-absorbent substrate 1 but released therefrom by contact with water, take place. When the mixture reaches the capture region 3, the first immunochemical component 2 immobilized on the water-absorbent substrate is bound to the analyte 9, thereby forming a complex 11 [water-absorbent substrate-first immunochemical component-analyte-second immunochemical component-first labeling substance-biotin-avidin-second labeling substance].

The complex 11 formed as described above can be visually confirmed, since the colored particles as a first labeling substance 5 and a second labeling substance 5 are assembled by higher order binding via avidin-biotin, so that the coloring is clear.

In the present invention, the water-absorbent substrate comprising a capture region in which a first immunochemical component is immobilized is also referred to as the immunological test strip of the present invention.

Further, the present invention provides in Embodiment C-1 the immunological test strip mentioned above and a kit for immunological detection method comprising the labeled components mentioned above and an avidin; in Embodiment C-2 the immunological test strip mentioned above and a kit for immunological detection method comprising the labeled components mentioned above and a conjugate comprising the biotin and a second labeling substance; and in Embodiment C-3 the immunological test strip mentioned above and a kit for immunological detection method comprising the labeled components mentioned above and a conjugate comprising the avidin and a second labeling substance. These kits of the present invention can be suitably used for the immunological detection methods of the present invention.

The immunological test strip and the labeled components contained in the kit of the present invention are as defined in the immunological detection method of the present invention mentioned above.

The avidin in Embodiment C-1, the conjugate comprising a biotin and the second labeling substance in Embodiment C-2, and the conjugate comprising an avidin and the second labeling substance, each contained in the kit of the present invention are as defined in the immunological detection method of the present invention mentioned above, and each is preferably maintained in a form capable of being released by contact with water in a given region between the capture region and one end of the water-absorbent substrate of the immunological test strip.

The present invention will be described in further detail by means of the following working examples, without by no means intending to limit the scope of the present invention thereto.

EXAMPLE A-1

Preparation of Kit for Immunological Detection
(1) Preparation of First Labeled Immunochemical Component Solution To 3 ml of a blue-colored carboxylated polystyrene latex particle dispersion [concentration: 5% by weight on a solid basis, average particle size: 0.1 $\mu$m, in 0.01 M borate buffer (pH 8)] were added 1 ml of a water-soluble carbodiimide [1 mg/ml, in 0.01 M borate buffer (pH 8)] and 1 ml of a 1 mg/ml goat IgG anti-*Escherichia coli* O157:H7 antibody [manufactured by Kirkegaard & Perry Laboratories Inc., in 0.01 M borate buffer (pH 8)]. The resulting mixture was allowed to react at 10° C. for 3 hours, and thereafter, the reaction mixture was washed by centrifugation using borate buffer (pH 8) as a washing solution, to prepare a blue-colored latex particle-labeled anti-*Escherichia coli* O157:H7 antibody. The resulting latex particle labeled antibody was suspended in 0.01 M-borate buffer (pH 8) so as to have a concentration of 2% by weight on a solid basis.
(2) Preparation of Second Labeled Immunochemical Component Solution In the same manner as described in the above item (1), to 3 ml of a blue-colored carboxylated polystyrene latex particle dispersion [concentration: 5% by weight on a solid basis, average particle size: 0.1 $\mu$m, in 0.01 M borate buffer (pH 8)] were added 1 ml of a water-soluble carbodiimide [1 mg/ml, in 0.01 M borate buffer (pH 8)] and 1 ml of a 2 mg/ml rabbit anti-goat IgG antibody [manufactured by Kirkegaard & Perry Laboratories Inc., in 0.01 M borate buffer (pH 8)]. The resulting mixture was allowed to react at 10° C. for 3 hours, and thereafter, the reaction mixture was washed by centrifugation using borate buffer (pH 8) as a washing solution, to prepare a blue-colored latex particle-labeled anti-goat IgG antibody. The resulting latex-labeled antibody was suspended in 0.01 M-borate buffer (pH 8) so as to have a concentration of 2% by weight on a solid basis.
(3) Preparation of Test Strip Using a dispenser, 0.5 $\mu$l of a 1 mg/ml rabbit IgG anti-*Escherichia coli* O157:H7 antibody [manufactured by Capricorn, in 0.1 M phosphate buffer (pH 7.4)] was applied in a linear form at a site of 30 mm from one end of a nitrocellulose membrane (pore size: 8 $\mu$m, 6 mm×60 mm). This membrane was immersed into an aqueous solution comprising 1% by weight of bovine serum albumin and 0.1% by weight of polyoxyethylene(10) octyl phenyl ether (manufactured by Wako Pure Chemical Industries, Ltd.) for 10 minutes, and thereafter dried at 40° C. for 2 hours.

Subsequently, to a reverse side of this membrane (opposite side to the antibody-coating surface) was adhered together a polyester film (100 $\mu$m thickness) using a spray glue. Further, at a site of 0 to 8 mm from the opposite end to the antibody-coating site was adhered together a polyester nonwoven fabric (6 mm×8 mm, 2.5 mm thickness), to prepare a test strip.

EXAMPLE A-2

Detection of *Escherichia coli* O157:H7 by Kit for Immunological Detection

There was prepared a liquid of a test sample obtained from dispersion of *Escherichia coli* O157:H7 strain in 0.1 M phosphate buffer (pH 7.4) containing 0.9% by weight NaCl at each concentration shown in Table A-1. The resulting liquid of a test sample was mixed with the first labeled antibody solution prepared in item (1) of Example A-1 so as to have a concentration of 0.02% by weight on a solid basis, and the mixture was stirred. Thereafter, 60 $\mu$l of a mixture was added dropwise to a polyester nonwoven fabric portion of the test strip prepared in item (3) of Example A-1. The mixture was developed on the test strip, and thereafter 60 $\mu$l of a diluted solution was added dropwise to the above polyester nonwoven fabric portion, the diluted solution being prepared by diluting the second labeled antibody solution prepared in item (2) of Example A-1 with 0.1 M phosphate buffer (pH 7.4) containing 0.9% by weight NaCl so as to have a concentration of 0.02% by weight on a solid basis. The presence or absence of coloring on a capture region after 20 minutes was visually observed. The results are shown in Table A-1. As a comparison, the assay results of the case where only the first labeled antibody was used without using a second labeled antibody are also given side by side.

EXAMPLE A-3

Detection of *Escherichia coli* O157:H7 by Kit for Immunological Detection

There was prepared a liquid of a test sample obtained from dispersion of *Escherichia coli* O157:H7 strain in 0.1 M phosphate buffer (pH 7.4) containing 0.9% by weight NaCl at each concentration shown in Table A-1. The resulting liquid of a test sample was mixed with the first labeled antibody solution prepared in item (1) of Example A-1 and the second labeled antibody solution prepared in item (2) of Example A-1 so as to have a concentration of 0.02% by weight each on a solid basis, and the mixture was stirred. Thereafter, 60 µl of the mixture was added dropwise to a polyester nonwoven fabric portion of the immunological test strip prepared in item (3) of Example A-1. The presence or absence of coloring on a capture region after 20 minutes was visually observed. The results are shown in Table A-1. As a comparison, the assay results of the case where only the first labeled antibody was used without using a second labeled antibody are also given side by side.

EXAMPLE A-4

Detection of *Escherichia coli* O157:H7 by Kit for Immunological Detection

There was prepared a test sample obtained from dispersion of *Escherichia coli* O157:H7 strain in 0.1 M phosphate buffer (pH 7.4) containing 0.9% by weight NaCl at each concentration shown in Table A-1. Two microliters of this test sample was allowed to absorb on the front side of the immunological test strip prepared in item (3) of Example A-1 at a site 12 to 20 mm from the opposite side to the antibody-applied site. Subsequently, the first labeled antibody solution prepared in item (1) of Example A-1 was diluted with 0.1 M phosphate buffer (pH 7.4) containing 0.9% by weight NaCl so as to have a concentration of 0.02% by weight on a solid basis. Thereafter, 60 µl of the dilution was added dropwise to a polyester nonwoven fabric portion of the test strip. The first labeled antibody solution was brought into contact with the test sample, and then developed. Thereafter, 60 µl of a diluted solution was added dropwise to the above polyester nonwoven fabric portion, the diluted solution being prepared by diluting the second labeled antibody solution prepared in item (2) of Example A-1 with 0.1 M phosphate buffer (pH 7.4) containing 0.9% by weight NaCl so as to have a concentration of 0.02% by weight on a solid basis. The presence or absence of coloring on a capture region after 20 minutes was visually observed. The results are shown in Table A-1. As a comparison, the assay results of the case where only the first labeled antibody was used without using a second labeled antibody are also given side by side.

EXAMPLE A-5

Detection of *Escherichia coli* O157:H7 by Kit for Immunological Detection

There was prepared a liquid of a test sample obtained from dispersion of *Escherichia coli* O157:H7 strain in 0.1 M phosphate buffer (pH 7.4) containing 0.9% by weight NaCl at each concentration shown in Table A-1. Two microliters of this test sample was allowed to absorb on the front side of the immunological test strip prepared in item (3) of Example A-1 at a site 12 to 20 mm from the opposite side to the antibody-applied site. Subsequently, the first labeled antibody solution prepared in item (1) of Example A-1 and the second labeled antibody solution prepared in item (2) of Example A-1 were mixed, and the resulting mixture was diluted with 0.1 M phosphate buffer (pH 7.4) containing 0.9% by weight NaCl so as to have a concentration of 0.02% by weight each on a solid basis. Thereafter, 60 µl of the mixed dilution was added dropwise to a polyester nonwoven fabric portion of the immunological test strip prepared in item (3) of Example A-1. The presence or absence of coloring on a capture region after 20 minutes was visually observed. The results are shown in Table A-1. As a comparison, the assay results of the case where only the first labeled antibody was used without using a second labeled antibody are also given side by side.

TABLE A-1

| Examples | Assay Method | O157:H7 Cell Density (cfu/ml) | | | | | | | |
|---|---|---|---|---|---|---|---|---|---|
| | | $10^8$ | $10^7$ | $10^6$ | $10^5$ | $10^4$ | $10^3$ | $10^2$ | 0 |
| A-2 | Using only first labeled antibody | + | + | + | + | − | − | − | − |
| | Using both first and second labeled antibodies | + | + | + | + | + | − | − | − |
| A-3 | Using only first labeled antibody | + | + | + | + | − | − | − | − |
| | Using both first and second labeled antibodies | + | + | + | + | + | − | − | − |
| A-4 | Using only first labeled antibody | + | + | + | − | − | − | − | − |
| | Using both first and second labeled antibodies | + | + | + | + | − | − | − | − |
| A-5 | Using only first labeled antibody | + | + | + | − | − | − | − | − |
| | Using both first and second labeled antibodies | + | + | + | + | − | − | − | − |

+: Coloring in the form of a line at a capture region is observed
−: Coloring in the form of a line at a capture region is not observed.

EXAMPLE B-1

Preparation of Constituents for Kit for Immunological Detection (1) Preparation of Colored Latex Comprising Water-Dispersible High-Molecular Polymeric Particles With stirring 50 g of styrene monomers, 0.5 g of acrylic acid, 0.2 g of triethylene glycol dimethacrylate, and 440 g of distilled water at a temperature of 75° C. under nitrogen stream, an aqueous solution was added thereto, the aqueous solution being prepared by dissolving 0.25 g of potassium persulfate in 10 g of water. The resulting mixture was polymerized for 10 hours to give an aqueous dispersion of water-dispersible high-molecular polymeric particles having an average particle size of 0.22 µm. The polymeric particle dispersion was washed by centrifugation sequentially with an alkali, an acid and distilled water, and thereafter adjusted so as to have a concentration of 10% by weight on a solid basis (carrier particle dispersion). In 20 ml of toluene was dissolved 0.2 g of Sudan blue, and to the resulting solution were added 0.2 g of sodium dodecyl sulfate and 100 ml of distilled water, and the mixture was emulsified by an ultrasonic dispersion machine. To the mixture was added 30 ml of the above carrier particle dispersion (concentration of 10% by weight on a solid basis), and the resulting mixture was stirred at room temperature for 24 hours. After removing toluene from this mixture on an evaporator, the resulting product was washed by centrifugation with 0.01 M borate buffer (pH 7.5) and adjusted so as to have a concentration of 5% by weight on a solid basis. To 50 ml of this mixture were added 5 ml of an aqueous solution of 1-ethyl-3-(3-dimethylaminopropyl)carbodiimide hydrochloride (10 mg/ml) and 50 ml of an aqueous solution of 0.03 M m-xylenediamine, and the resulting mixture was allowed to react at room temperature for 5 hours. This resulting mixture was heat-treated at 75° C. for 5 hours, and thereafter washed by centrifugation with the same buffer as above, and adjusted so as to have a concentration of 1% by weight on a solid basis (Sudan blue-stained xylenediamine-spacer particle dispersion).

(2) Preparation of Solution Comprising First Labeled Component

To 10 ml of Sudan blue-stained xylenediamine-spacer particle dispersion prepared in the above item (1) was added 1 ml of an aqueous solution of glutaraldehyde (0.1 mg/ml), and the resulting mixture was allowed to react at room temperature for 2 hours. Thereafter, the reaction mixture was washed by centrifugation with the same buffer as above, and adjusted to a dispersion having a concentration of 1% by weight on a solid basis. To 10 ml of this dispersion were added respectively 1 ml of an anti-human hemoglobin antibody (rabbit IgG, 10 mg/ml) as a third immunochemical component and 1 ml of an anti-human HBs antibody (rabbit IgG, 5 mg/ml) as a second immunochemical component, and the resulting mixture was stirred at 10° C. for 24 hours. The resulting mixture was washed by centrifugation with the same buffer as above, and re-dispersed so as to have a concentration of 1% by weight on a solid basis, to give a solution comprising Sudan blue-stained particle-labeled anti-human hemoglobin antibody-anti-human HBs antibody (first labeled component), in which the antibodies are bound by covalent bonding.

(3) Preparation of Solution Comprising Second Labeled Component

To 10 ml of Sudan blue-stained xylenediamine-spacer particle dispersion prepared in the above item (1) was added 1 ml of an aqueous solution of glutaraldehyde (0.1 mg/ml), and the resulting mixture was allowed to react at room temperature for 2 hours. Thereafter, the reaction mixture was washed by centrifugation with the same buffer as above, and adjusted to a dispersion having a concentration of 1% by weight on a solid basis. To 10 ml of this dispersion was added 2 ml of an anti-human hemoglobin antibody (rabbit IgG, 10 mg/ml) as a fourth immunochemical component, and the resulting mixture was stirred at 10° C. for 24 hours. The resulting mixture was washed by centrifugation with the same buffer as above, and re-dispersed so as to have a concentration of 1% by weight on a solid basis, to give a solution comprising Sudan blue-stained particle-labeled anti-human hemoglobin antibody (second labeled component), in which the antibodies are bound by covalent bonding.

(4) Preparation of Immunological Test Strip

Anti-human HBs antibodies (rabbit IgG) as a first immunochemical component were diluted with 0.1 M phosphate buffer (pH 7.4), to adjust to an aqueous solution having a final concentration of 1 mg/ml. Ten microliters of this aqueous solution was applied to a site 50 mm from one end of a nitrocellulose membrane filter (Toyo Filter Paper, 5×100 mm), and thereafter the resulting filter was immediately allowed to stand at 37° C. for 1 hour. Thereafter, the nitrocellulose membrane filter was taken out, and immersed into an aqueous solution of 0.1% bovine serum albumin and 0.1% Tween 20 for 1 hour. Subsequently, the nitrocellulose membrane filter was taken out, and allowed to stand at room temperature for 3 hours, to give a nitrocellulose membrane filter carrying anti-human HBs antibodies. Next, a separation region for hematocyte (Toyo Filter Paper No.2, 5×10 mm) was positioned near one end (solution-absorbing site) of the test strip of the above anti-human HBs antibody-immobilized nitrocellulose membrane filter, to give a test strip comprising a nitrocellulose membrane filter comprising a capture region and a separation region for hematocyte.

(5) Preparation of Immunological Test Strip in which Reagent Region is Positioned To 1 ml of an aqueous solution of 5% by weight polyvinyl pyrrolidone (viscosity-average molecular weight: 25,000) was added 0.1 ml of the solution comprising the first labeled component prepared in item (2) of Example B-1, and the resulting mixture was thoroughly mixed. Thereafter, 10 μl of this solution was applied at a site 20 to 30 mm from the capture region of the above test strip, and the resulting test strip was dried in a desiccator for 2 days, to give an immunological test strip in which a reagent region is positioned.

EXAMPLE B-2

Detection of Human HBs Antigen by Kit for Immunological Detection

Figure 5:
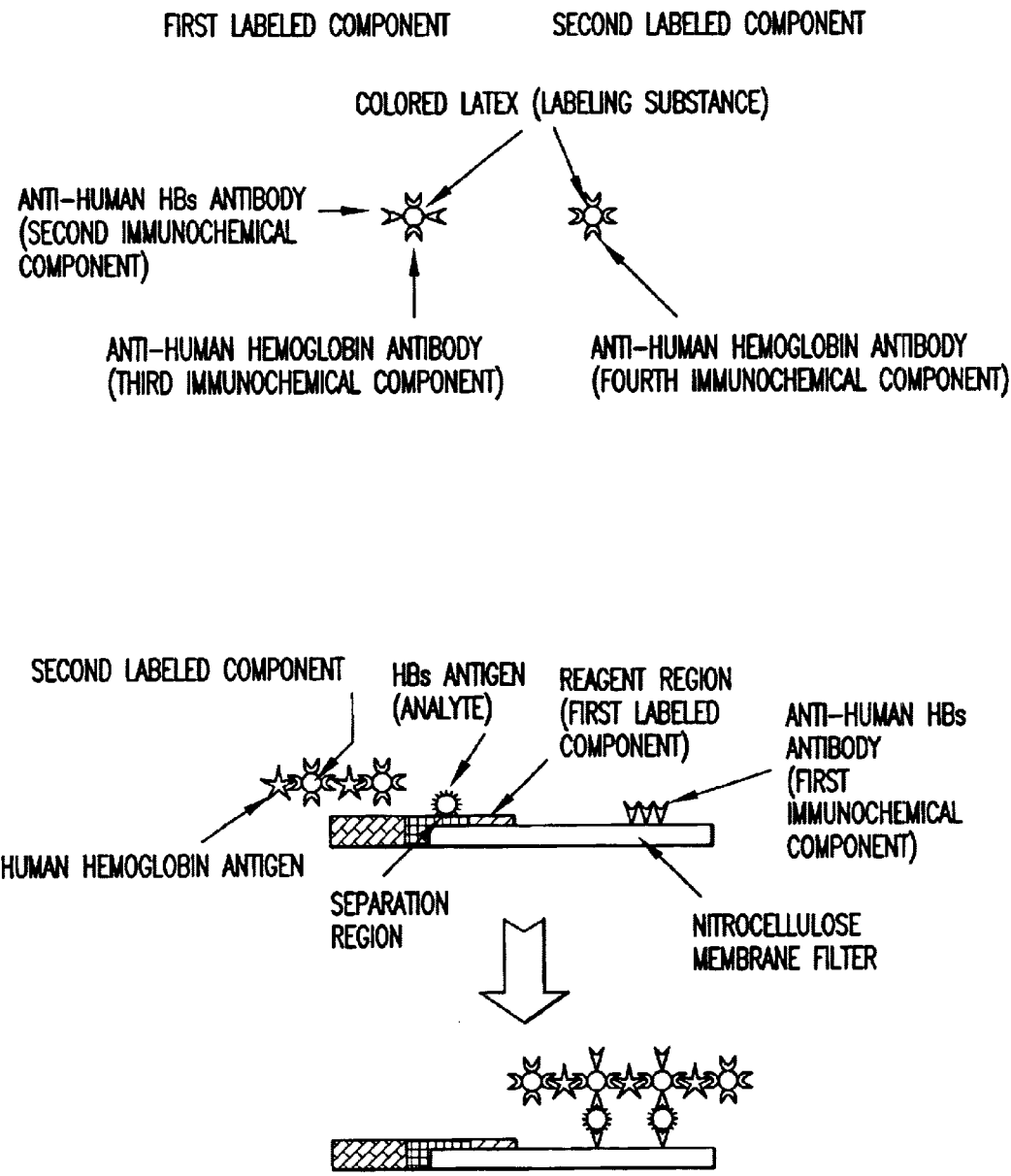
FIG. 5 is a schematic view showing the manner of antigen-antibody reaction in each step of assay of human HBs antigen using the immunological detection kit of the present invention (Embodiment B-1).

To the separation region for hematocyte of the test strip prepared in item (5) of Example B-1 was added dropwise 10 μl of a liquid of a test sample prepared by dissolving human HBs antigens in a physiological saline. Immediately thereafter, 100 μl of a mixture of a solution comprising hemoglobin antigens (protein concentration: 200 ng/ml) and the solution comprising the second labeled component (concentration on a solid basis: 0.2% by weight) prepared in item (3) of Example B-1 was added dropwise to the solution-absorbing site, and then developed. The coloring on a capture region after 10 minutes was visually observed (FIG. 5). The results are shown in Table B-1.

TABLE B-1

| Concentration of HBs Antigen ng/ml | Evaluation Results |
| --- | --- |
| 0 | − |
| 1 | ± |
| 5 | ± |
| 10 | ± |
| 50 | ± |
| 100 | + |
| 1,000 | + |
| 10,000 | + |
| 100,000 | + |

−: No coloring;
±: slight coloring; and
+: intensive coloring.

Comparative Example B-1

To the separation region for hematocyte of the test strip prepared in item (4) of Example B-1 was added dropwise 10 μl of a liquid of a test sample prepared by dissolving human HBs antigens in a physiological saline. Immediately thereafter, 50 μl of the solution comprising the first labeled component prepared in item (2) of Example B-1 (concentration on a solid basis: 0.2% by weight) was added dropwise to the solution-absorbing site, and then developed. After 10 minutes, 100 μl of a solution comprising hemoglobin antigens (protein concentration: 200 ng/ml) was added dropwise to the solution-absorbing site, and then developed. After additional 10 minutes, 50 μl of the solution comprising the second labeled component prepared in item (3) of Example B-1 (concentration on a solid basis: 0.2% by weight) was added dropwise to the solution-absorbing site, and then developed. The coloring on a capture region after 10 minutes was visually observed. The results are shown in Table B-2.

TABLE B-2

| Concentration of HBs Antigen ng/ml | Evaluation Results | | |
|---|---|---|---|
| | After Addition of First Labeled Component | After Addition of Hb Antigen | After Addition of Second Labeled Component |
| 0 | - | - | - |
| 1 | - | - | ± |
| 5 | - | - | ± |
| 10 | ± | ± | ± |
| 50 | ± | ± | ± |
| 100 | ± | ± | + |
| 1,000 | ± | ± | + |
| 10,000 | + | + | + |
| 100,000 | + | + | + |

-: No coloring;
±: slight coloring; and
+: intensive coloring.

EXAMPLE B-3

Detection of Human HBs Antigen by Kit for Immunological Detection

Figure 6:
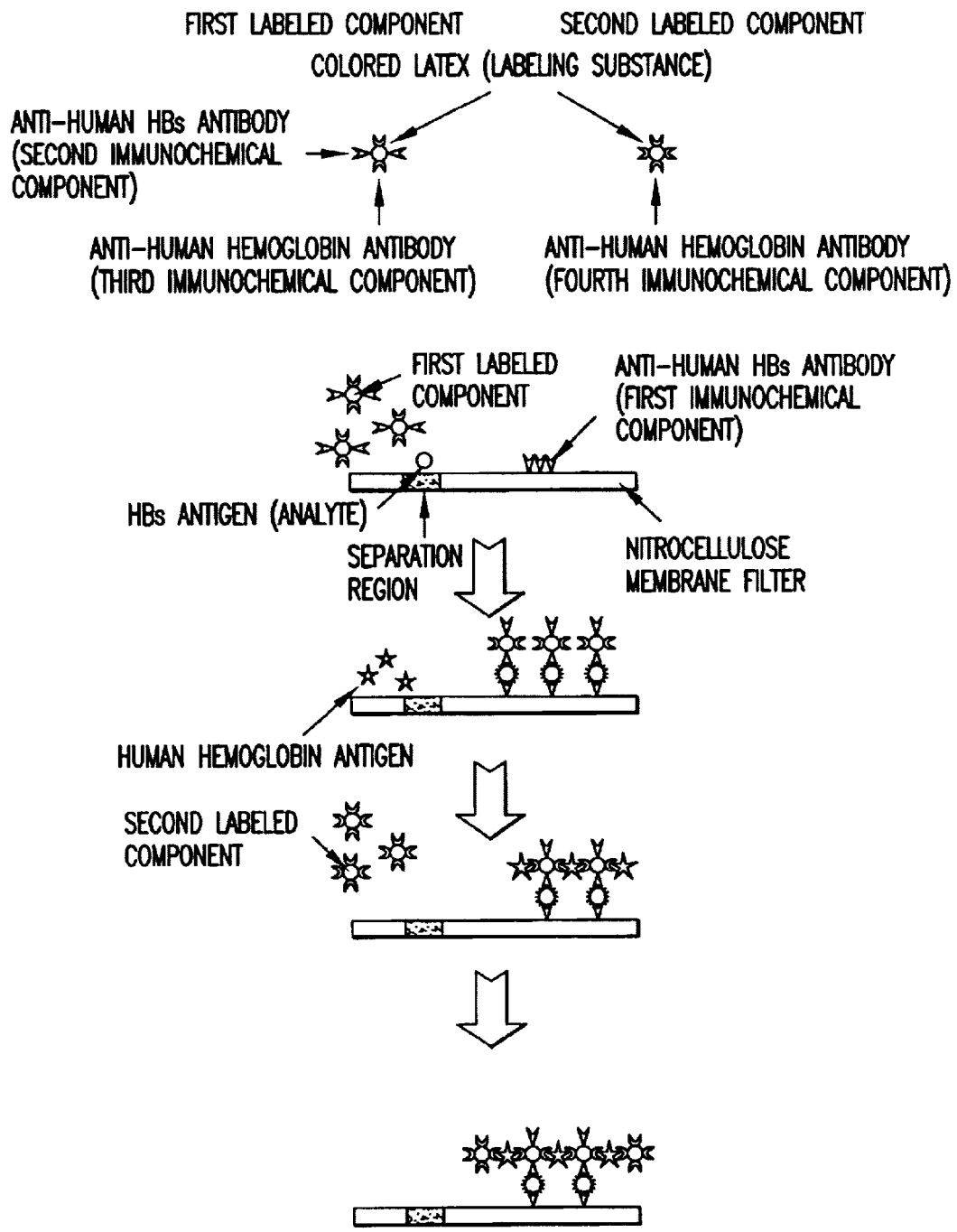
FIG. 6 is a schematic view showing the manner of antigen-antibody reaction in each step of assay of human HBs antigen using the immunological detection kit of the present invention (Embodiment B-2).

To the separation region for hematocyte of the test strip prepared in item (4) of Example B-1 was added dropwise 10 µl of a liquid of a test sample prepared by dissolving human HBs antigens in a physiological saline. Immediately thereafter, 50 µl of the solution comprising the first labeled component prepared in item (2) of Example B-1 (concentration on a solid basis: 0.2% by weight) was added dropwise to the solution-absorbing site, and then developed. After 10 minutes, 100 µl of a solution comprising hemoglobin antigens (protein concentration: 200 ng/ml) was added dropwise to the solution-absorbing site, and then developed. After additional 10 minutes, 50 µl of the solution comprising the second labeled component prepared in item (3) of Example B-1 (concentration on a solid basis: 0.2% by weight) was added dropwise to the solution-absorbing site, and then developed (FIG. 6). The coloring on a capture region after 10 minutes was visually observed. The results are shown in Table B-3.

TABLE B-3

| Concentration of HBs Antigen ng/ml | Evaluation Results |
|---|---|
| 0 | - |
| 1 | ± |
| 5 | ± |
| 10 | ± |
| 50 | ± |
| 100 | + |
| 1,000 | + |
| 10,000 | + |
| 100,000 | + |

-: No coloring;
±: slight coloring; and
+: intensive coloring.

Comparative Example B-2

To the separation region for hematocyte of the test strip prepared in item (4) of Example B-1 was added dropwise 10 µl of a liquid of a test sample prepared by dissolving human HBs antigens in a physiological saline. Immediately thereafter, 50 µl of the solution comprising the first labeled component prepared in item (2) of Example B-1 (concentration on a solid basis: 0.2% by weight) was added dropwise to the solution-absorbing site, and then developed. The coloring on a capture region after 10 minutes was visually observed. The results are shown in Table B-4.

TABLE B-4

| Concentration of HBs Antigen ng/ml | Evaluation Results After Addition of First Labeled Component |
|---|---|
| 0 | - |
| 1 | - |
| 5 | - |
| 10 | ± |
| 50 | ± |
| 100 | ± |
| 1,000 | ± |
| 10,000 | + |
| 100,000 | + |

-: No coloring;
±: slight coloring; and
+: intensive coloring.

EXAMPLE B-4

Detection of Human HBs Antigen by Kit for Immunological Detection

Figure 7:
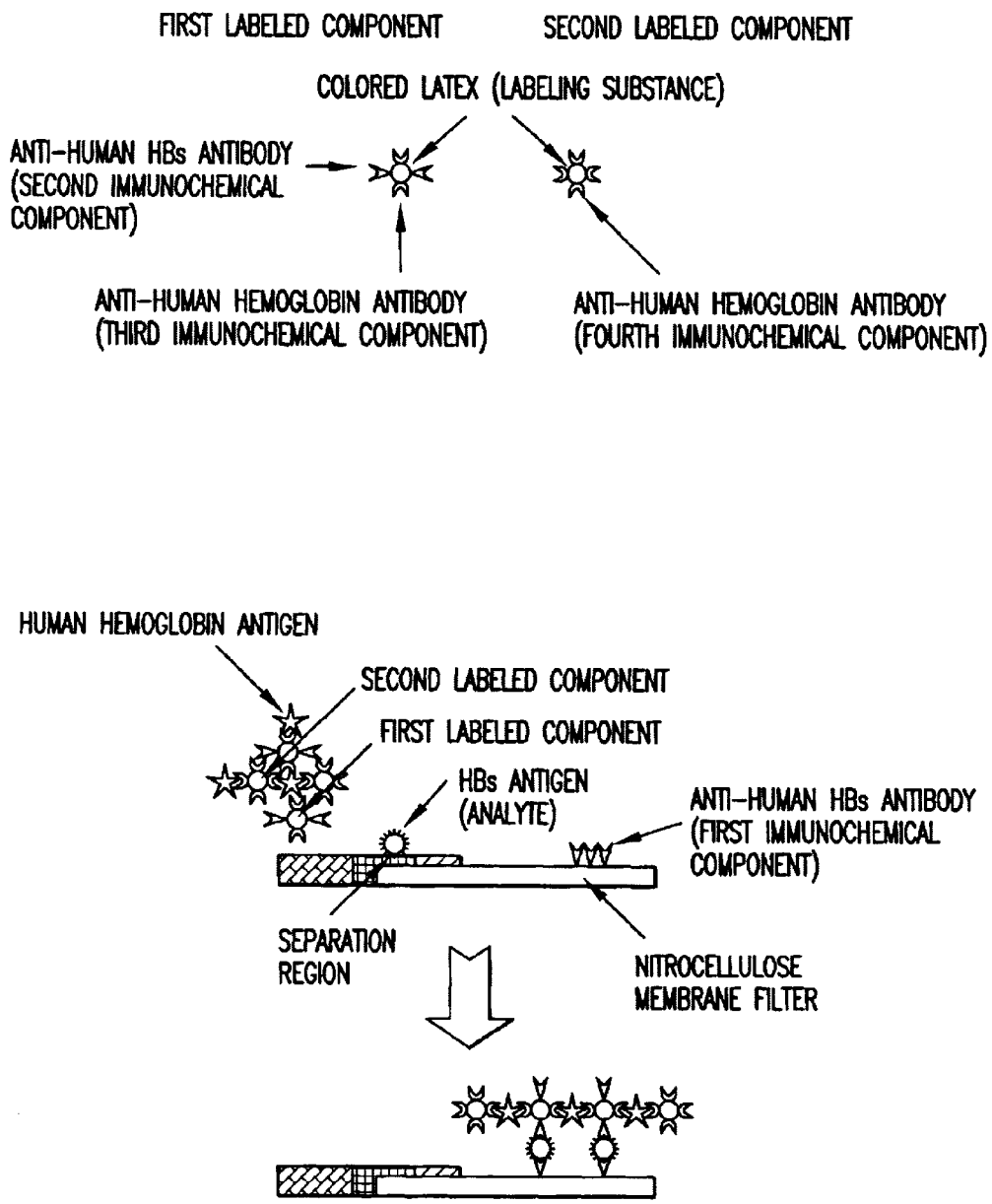
FIG. 7 is a schematic view showing the manner of antigen-antibody reaction in each step of assay of human HBs antigen using the immunological detection kit of the present invention (Embodiment B-3).

To the separation region for hematocyte of the test strip prepared in item (4) of Example B-1 was added dropwise 10 µl of a liquid of a test sample prepared by dissolving human HBs antigens in a physiological saline. Immediately thereafter, 100 µl of a mixture of the solution comprising the first labeled component prepared in item (2) of Example B-1 (concentration on a solid basis: 0.2% by weight), the solution comprising hemoglobin antigens (protein concentration: 200 ng/ml) and the solution comprising the second labeled component prepared in item (3) of Example B-1 (concentration on a solid basis: 0.2% by weight) was added dropwise to the solution-absorbing site, and then developed. The coloring on a capture region after 10 minutes was visually observed (FIG. 7). The results are shown in Table B-5.

TABLE B-5

| Concentration of HBs Antigen ng/ml | Evaluation Results |
|---|---|
| 0 | - |
| 1 | ± |
| 5 | ± |
| 10 | ± |
| 50 | ± |
| 100 | + |
| 1,000 | + |
| 10,000 | + |
| 100,000 | + |

-: No coloring;
±: slight coloring; and
+: intensive coloring.

Comparative Example B-3

To the separation region for hematocyte of the test strip prepared in item (4) of Example B-1 was added dropwise 10 µl of a liquid of a test sample prepared by dissolving human HBs antigens in a physiological saline. Immediately thereafter, 50 µl of the solution comprising the first labeled component prepared in item (2) of Example B-1 (concentration on a solid basis: 0.2% by weight) was added dropwise to the solution-absorbing site, and then developed. After 10 minutes, 100 µl of a solution comprising hemoglobin antigens (protein concentration: 200 ng/ml) was added dropwise to the solution-absorbing site, and then developed. After additional 10 minutes, 50 µl of the solution comprising the second labeled component prepared in item (3) of Example B-1 (concentration on a solid basis: 0.2% by weight) was added to the solution-absorbing site, and then developed. The coloring on a capture region after 10 minutes was visually observed. The results are shown in Table B-6.

TABLE B-6

| Concentration of HBs Antigen ng/ml | Evaluation Results | | |
|---|---|---|---|
| | After Addition of First Labeled Component | After Addition of Hb Antigen | After Addition of Second Labeled Component |
| 0 | − | − | − |
| 1 | − | − | ± |
| 5 | − | − | ± |
| 10 | ± | ± | ± |
| 50 | ± | ± | ± |
| 100 | ± | ± | + |
| 1,000 | ± | ± | + |
| 10,000 | + | + | + |
| 100,000 | + | + | + |

−: No coloring;
±: slight coloring; and
+: intensive coloring.

EXAMPLE B-5

Preparation of Immunological Test Strip in which Reagent Region Is Positioned

To 1 ml of an aqueous solution of 5% by weight polyvinyl pyrrolidone (viscosity-average molecular weight: 25,000) was added 0.1 ml of the solution comprising the second labeled component prepared in item (3) of Example B-1, and the resulting mixture was thoroughly mixed. Thereafter, 10 µl of this solution was applied to a site 20 to 30 mm from the capture region of the above test strip of item (4) of Example B-1, and the resulting test strip was dried in a desiccator for 2 days, to give an immunological test strip in which a reagent region is positioned.

EXAMPLE B-6

Detection of Human HBs Antigen by Kit for Immunological Detection

Figure 8:
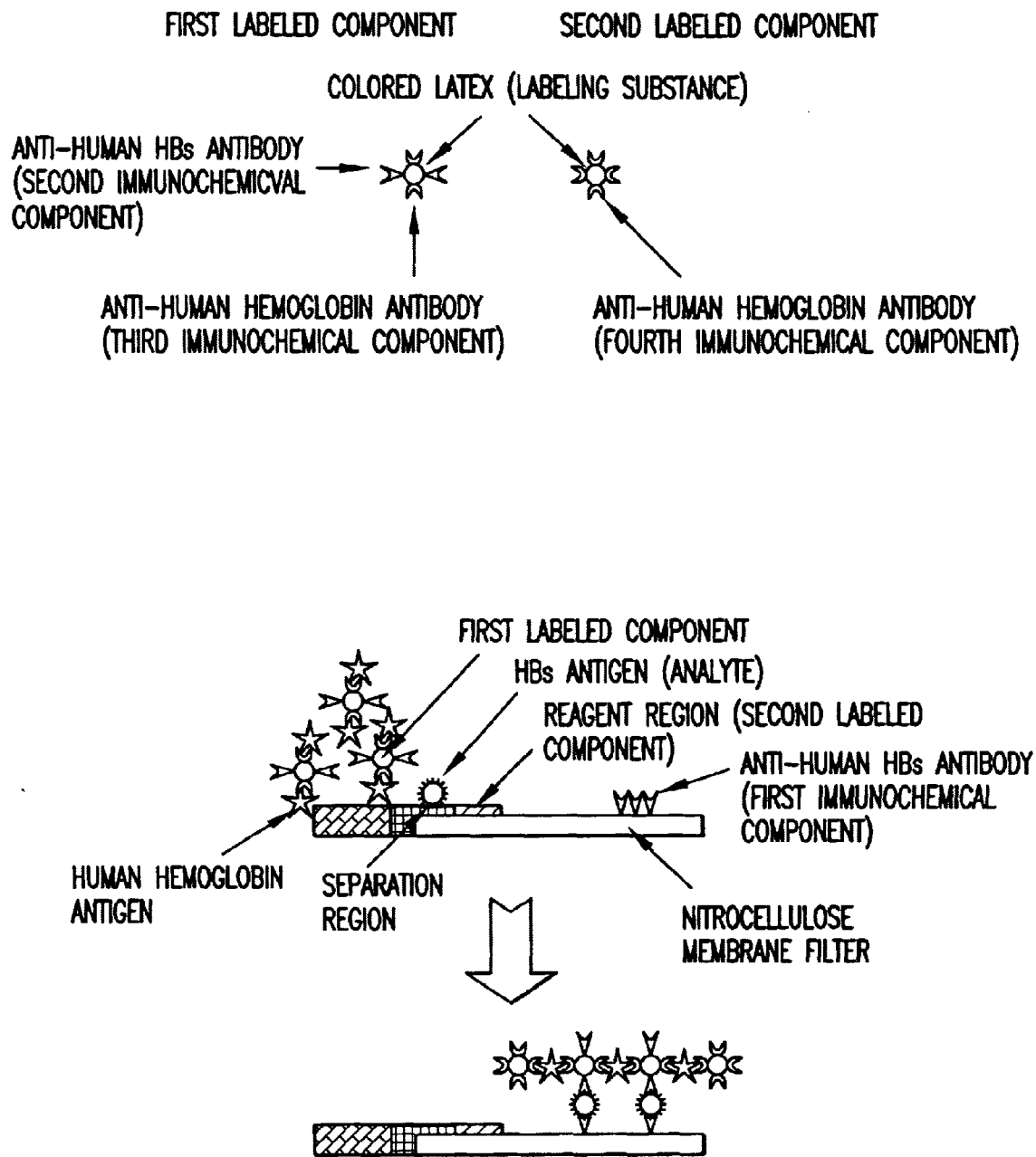
FIG. 8 is a schematic view showing the manner of antigen-antibody reaction in each step of assay of human HBs antigen using the immunological detection kit of the present invention (Embodiment B-4).

To the separation region for hematocyte of the test strip prepared in Example B-5 was added dropwise 10 µl of a liquid of a test sample prepared by dissolving human HBs antigens in a physiological saline. Immediately thereafter, 100 µl of a mixture of the solution comprising hemoglobin antigens (protein concentration: 200 ng/ml) and the solution comprising the first labeled component prepared in item (2) of Example B-1 (concentration on a solid basis: 0.2% by weight) was added dropwise to the solution-absorbing site, and then developed. The coloring on a capture region after 10 minutes was visually observed (FIG. 8). The results are shown in Table B-7.

TABLE B-7

| Concentration of HBs Antigen ng/ml | Evaluation Results | | |
|---|---|---|---|
| | After Addition of First Labeled Component | After Addition of Hb Antigen | After Addition of Second Labeled Component |
| 0 | − | − | − |
| 1 | − | − | ± |
| 5 | − | − | ± |
| 10 | ± | ± | ± |
| 50 | ± | ± | ± |
| 100 | ± | ± | + |
| 1,000 | ± | ± | + |
| 10,000 | + | + | + |
| 100,000 | + | + | + |

−: No coloring;
±: slight coloring; and
+: intensive coloring.

Comparative Example B-4

An assay for human Hbs antigen was carried out in the same manner as in Example B-6 except for using only the first labeled component prepared in item (2) of Example B-1 without using second labeled component or hemoglobin antigens which were a mediating substance. Specifically, to the separation region for hematocyte of the test strip prepared in Example B-5 was added dropwise 10 µl of a liquid of a test sample prepared by dissolving human HBs antigens in a physiological saline. Immediately thereafter, 50 µl of the solution comprising the first labeled component (concentration on a solid basis: 0.2% by weight) was added dropwise to the solution-absorbing site, and then developed. The coloring on a capture region after 10 minutes was visually observed. The results are shown in Table B-8.

TABLE B-8

| Concentration of HBs Antigen ng/ml | After Addition of First Labeled Component |
|---|---|
| 0 | − |
| 1 | − |
| 5 | − |
| 10 | ± |
| 50 | ± |
| 100 | ± |
| 1,000 | ± |
| 10,000 | + |
| 100,000 | + |

−: No coloring;
±: slight coloring; and
+: intensive coloring.

EXAMPLE B-7

Preparation of Immunological Test Strip in which Reagent Region Is Positioned

To 1 ml of an aqueous solution of 5% by weight polyvinyl pyrrolidone (viscosity-average molecular weight: 25,000) was added 0.1 ml each of the solution comprising the first labeled component prepared in item (2) of Example B-1 and the solution comprising the second labeled component prepared in item (3) of Example B-1, and the resulting mixture was thoroughly mixed. Thereafter, 10 µl of the resulting mixture was applied to a site 40 to 50 mm from the capture region of the above test strip of item (4) of Example B-1, and the resulting test strip was dried in a desiccator for 2 days, to give an immunological test strip in which a reagent region is positioned.

EXAMPLE B-8

Detection of Human HBs Antigen by Kit for Immunological Detection

Figure 9:
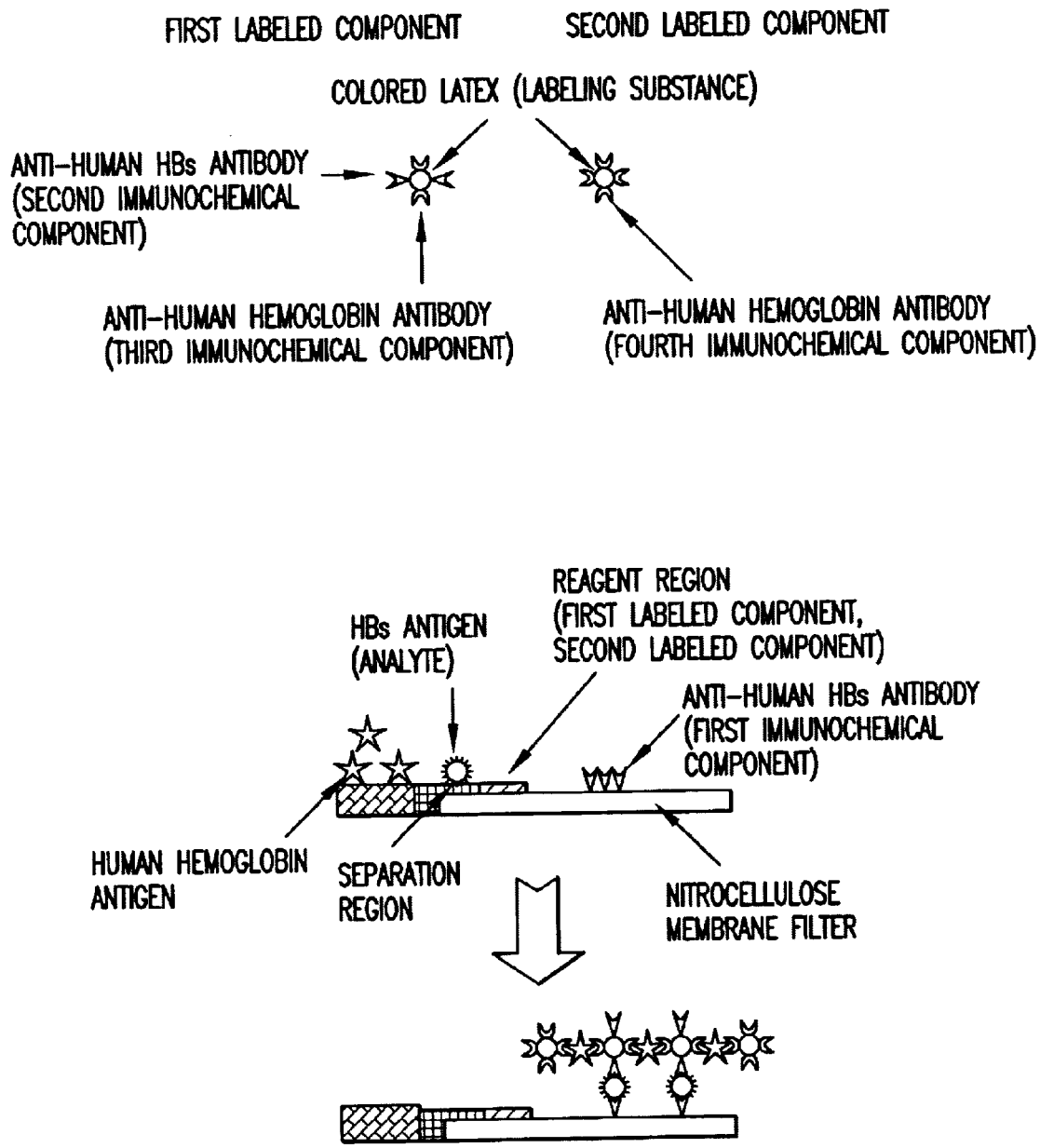
FIG. 9 is a schematic view showing the manner of antigen-antibody reaction in each step of assay of human HBs antigen using the immunological detection kit of the present invention (Embodiment B-5).

To the separation region for hematocyte of the test strip prepared in Example B-7 was added dropwise 10 µl of a liquid of a test sample prepared by dissolving human HBs antigens in a physiological saline. Immediately thereafter, 100 µl of the solution comprising hemoglobin antigens (protein concentration: 200 ng/ml) was added dropwise to the solution-absorbing site, and then developed. The coloring on a capture region after 10 minutes was visually observed (FIG. 9). The results are shown in Table B-9.

TABLE B-9

| Concentration of HBs Antigen ng/ml | Evaluation Results |
|---|---|
| 0 | − |
| 1 | ± |
| 5 | ± |
| 10 | ± |
| 50 | ± |
| 100 | + |
| 1,000 | + |
| 10,000 | + |
| 100,000 | + |

−: No coloring;
±: slight coloring; and
+: intensive coloring.

Comparative Example B-5

To the separation region for hematocyte of the test strip prepared in Example B-7 was added dropwise 10 µl of a liquid of a test sample prepared by dissolving human HBs antigens in a physiological saline. Immediately thereafter, 50 µl of the solution comprising the first labeled component (concentration on a solid basis: 0.2% by weight) prepared in item (2) of Example B-1 was added dropwise to the solution-absorbing site, and then developed. After 10 minutes, 100 µl of a solution comprising hemoglobin antigens (protein concentration: 200 ng/ml) was added dropwise to the solution-absorbing site, and then developed. After additional 10 minutes, 50 µl of the solution comprising the second labeled component prepared in item (3) of Example B-1 (concentration on a solid basis: 0.2% by weight) was added to the solution-absorbing site, and then developed. The coloring on a capture region after 10 minutes was visually observed.

The results are shown in Table B-10.

TABLE B-10

| | Evaluation Results | | |
|---|---|---|---|
| Concentration of HBs Antigen ng/ml | After Addition of First Labeled Component | After Addition of Hb Antigen | After Addition of Second Labeled Component |
| 0 | − | − | − |
| 1 | − | − | ± |
| 5 | − | − | ± |
| 10 | ± | ± | ± |
| 50 | ± | ± | ± |
| 100 | ± | ± | + |
| 1,000 | ± | ± | + |
| 10,000 | + | + | + |
| 100,000 | + | + | + |

−: No coloring;
±: slight coloring; and
+: intensive coloring.

EXAMPLE C-1

[Preparation of Water-Dispersible High-Molecular Polymeric Particles]

With stirring 50 g of styrene monomers, 0.5 g of acrylic acid, 0.2 g of triethylene glycol dimethacrylate, and 440 g of distilled water at a temperature of 75° C. under nitrogen stream, an aqueous solution prepared by dissolving 0.25 g of potassium persulfate in 10 g of water was added to the stirred mixture. The resulting mixture was polymerized for 10 hours to give an aqueous dispersion of water-dispersible high-molecular polymeric particles having an average particle size of 0.22 µm.

The resulting polymeric particle dispersion was washed by centrifugation sequentially with an alkali, an acid and distilled water, and thereafter adjusted so as to have a concentration of 10% by weight on a solid basis (carrier particle dispersion).

A 0.2 g Sudan blue was dissolved in 20 ml of toluene, and 0.2 g of sodium dodecyl sulfate and 100 ml of distilled water were added thereto. Thereafter, the resulting mixture was emulsified by an ultrasonic dispersion machine.

Thirty milliliters of the above carrier particle dispersion (concentration of 10% by weight on a solid basis) was added to the obtained emulsion, and the resulting mixture was stirred at room temperature for 24 hours. After removing toluene from this mixture with an evaporator, the resulting product was washed by centrifugation with 0.01 M borate buffer (pH 7.5) and adjusted so as to have a concentration of 5% by weight on a solid basis.

To 50 ml of this mixture were added 5 ml of an aqueous solution of 1-ethyl-3-(3-dimethylaminopropyl)carbodiimide hydrochloride (10 mg/ml) and 50 ml of an aqueous solution of 0.03 M m-xylenediamine. After reacting the resulting mixture at room temperature for 5 hours, the reacted mixture was heat-treated at 75° C. for 5 hours. Thereafter, the resulting mixture was washed by centrifugation with the same buffer as above, and adjusted so as to have a concentration of 1% by weight on a solid basis (Sudan blue-stained xylenediamine-spacer particle dispersion).

[Preparation of Labeled Component]

To 10 ml of the above Sudan blue-stained xylenediamine-spacer particle dispersion was added 1 ml of an aqueous solution of glutaraldehyde (0.1 mg/ml), and the resulting mixture was allowed to react at room temperature for 2 hours. Thereafter, the reaction mixture was washed by centrifugation with the same buffer as above, and adjusted to a dispersion having a concentration of 1% by weight on a solid basis. To 10 ml of the obtained dispersion were added 1 mg of biocytin and 1 ml of an anti-human HBs antibody (rabbit IgG, 5 mg/ml), and the resulting mixture was stirred at 10° C. for 24 hours. The resulting mixture was washed by centrifugation with the same buffer as above, and re-dispersed so as to have a concentration of 1% by weight on a solid basis, to give a Sudan blue-stained particle-labeled biocytin-anti-human HBs antibody (labeled component), in which the antibodies are bound by covalent bonding.

[Preparation of Capture Region]

Anti-human HBs antibodies (rabbit IgG) were diluted with 0.1 M phosphate buffer (pH 7.4), to prepare an aqueous solution having a final concentration of 1 mg/ml. Ten microliters of this aqueous solution was applied to a site of 2 cm from one end of a nitrocellulose membrane filter (Toyo Filter Paper, 5×100 mm), and immediately thereafter the resulting filter was allowed to stand at 37° C. for 1 hour. Thereafter, the nitrocellulose membrane filter was taken out, and immersed into an aqueous solution of 0.1% bovine serum albumin and 0.1% Tween 20 for 1 hour.

Subsequently, the nitrocellulose membrane filter was taken out, and allowed to stand at room temperature for 3 hours with air-drying, to give a nitrocellulose membrane filter (immunological test strip) having a capture region in which the anti-human HBs antibodies were immobilized and at one end of the filter a receiver of nonwoven fabric (5 mm×10 mm).

[Detection of Human HBs]

A test sample prepared by dissolving human HBs antigens in a physiological saline, the labeled components, and a mixture comprising avidin (concentration on a solid basis: 0.2% by weight) were mixed, and 100 μl of this mixture was added dropwise from one end of the above immunological test strip (receiver), and then developed. The coloring on a capture region after 20 minutes was observed. The results are shown in Table C-1.

EXAMPLE C-2

A Sudan blue-stained particle-labeled biocytin-anti-human HBs antibody (labeled component) was obtained in the same manner as in Example C-1.

[Preparation of Capture Region and Avidin Region]

Anti-human HBs antibodies (rabbit IgG) were diluted with 0.1 M phosphate buffer (pH 7.4), to prepare an aqueous solution having a final concentration of 1 mg/ml. Ten microliters of this aqueous solution was applied to a site of 2 cm from one end of a nitrocellulose membrane filter (Toyo Filter Paper, 5×100 mm), and immediately thereafter the resulting filter was allowed to stand at 37° C. for 1 hour. Thereafter, the nitrocellulose membrane filter was taken out, and immersed into an aqueous solution of 0.1% bovine serum albumin and 0.1% Tween 20 for 1 hour.

Subsequently, the nitrocellulose membrane filter was taken out, and allowed to stand at room temperature for 3 hours, to give a nitrocellulose membrane filter (immunological test strip) having a capture region in which the anti-human HBs antibodies were immobilized and at one end of the filter a receiver of nonwoven fabric (5 mm×10 mm). Thereafter, 10 μl of a solution prepared by dissolving avidin (1 mg/ml) in 0.1 M phosphate buffer (pH 7.4) was applied to a part between the capture region and receiver of the above immunological test strip, and immediately thereafter, the resulting test strip was allowed to stand at 37° C. for 1 hour, to give an immunological test strip comprising an avidin region.

[Detection of Human HBs]

From one end on the avidin region-side of the above immunological test strip, 100 μl of a mixture of a test sample prepared by dissolving human HBs antigens in a physiological saline, and the labeled components (concentration on a solid basis: 0.2% by weight) was added dropwise to the receiver, and then developed. The coloring on a capture region after 20 minutes was observed.

The results are shown in Table C-1.

TABLE C-1

| Concentration of HBs Antigen ng/ml | Evaluation Results Example C-1 | Evaluation Results Example C-2 |
|---|---|---|
| 0 | − | − |
| 0.25 | ± | ± |
| 0.5 | ± | ± |
| 1 | ± | ± |
| 5 | + | + |
| 10 | + | + |
| 100 | + | + |
| 1,000 | + | + |
| 10,000 | + | + |

−: No coloring;
±: slight coloring; and
+: intensive coloring.

From Table C-1, the detection sensitivity for human HBs antigen according to the immunological method of the present invention was about 0.25 ng/ml.

Comparative Example C-1

In the same manner as in Example C-1, there were obtained a nitrocellulose membrane filter in which the anti-human HBs antibodies were immobilized, and a Sudan blue-stained particle-labeled anti-human HBs antibody (labeled component).

From one end of the test strip comprising the above nitrocellulose membrane filter, 100 μl of a mixture of a test sample prepared by dissolving human HBs antigens in a physiological saline and the labeled components (concentration on a solid basis: 0.2% by weight) was added dropwise. The coloring on a capture region after 20 minutes was observed. The results are shown in Table C-2.

TABLE C-2

| Concentration of HBs Antigen ng/ml | Evaluation Results Comparative Example C-1 |
|---|---|
| 0 | − |
| 0.25 | − |
| 0.5 | − |
| 1 | − |
| 5 | − |
| 10 | ± |
| 100 | ± |
| 1,000 | + |
| 10,000 | + |

−: No coloring;
±: slight coloring; and
+: intensive coloring.

From Table C-2, the detection sensitivity for human HBs antigen according to the immunological method of the comparative example was about 10 ng/ml. Therefore, it is found that the sensitivity of the immunological method of the present invention increases about 40 times compared to a conventional method.

EXAMPLE C-3

[Preparation of Labeled Component]

One milliliter of an aqueous solution of glutaraldehyde (0.1 mg/ml) was added to 10 ml of a Sudan blue-stained xylenediamine-spacer particle dispersion obtained in the same manner as in Example C-1, and the resulting mixture was allowed to react at room temperature for 2 hours. Thereafter, the resulting reaction mixture was washed by centrifugation with the same buffer as in Example C-1, and adjusted to a dispersion having a concentration of 1% by weight on a solid basis. To 10 ml of the obtained dispersion were added 1 mg of avidin and 1 ml of an anti-human HBs antibody (rabbit IgG, 5 mg/ml), and the resulting mixture was stirred at 10° C. for 24 hours. The resulting mixture was washed by centrifugation with the same buffer as above, and re-dispersed so as to have a concentration of 1% by weight on a solid basis, to give a Sudan blue-stained particle-labeled avidin-anti-human HBs antibody (labeled component), in which the antibodies are bound by covalent bonding.

[Preparation of Conjugate Comprising Biotin and Second Labeling Substance]

One milliliter of an aqueous solution of glutaraldehyde (0.1 mg/ml) was added to 10 ml of a Sudan blue-stained xylenediamine-spacer particle dispersion obtained in the same manner as in Example C-1, and the resulting mixture was allowed to react at room temperature for 2 hours. Thereafter, the resulting reaction mixture was washed by centrifugation with the same buffer as in Example C-1, and adjusted to a dispersion having a concentration of 1% by weight on a solid basis. To 10 ml of this dispersion was added 1 mg of biotin, and the resulting mixture was stirred at 10° C. for 24 hours. The resulting mixture was washed by centrifugation with the same buffer as above, and re-dispersed so as to have a concentration of 1% by weight on a solid basis, to give a Sudan blue-stained particle-labeled biotin (conjugate comprising biotin and the second labeling substance), in which biotin is bound by covalent bonding.

[Preparation of Capture Region]

In the same manner as in Example C-1, there was obtained a nitrocellulose membrane filter (immunological test strip) having a capture region in which the anti-human HBs antibodies were immobilized and at one end a receiver of nonwoven fabric (5×10 mm).

[Detection of Human HBs]

A test sample prepared by dissolving human HBs antigens in a physiological saline, the labeled components (concentration on a solid basis: 0.2% by weight), and the conjugate comprising biotin and a second labeling substance (concentration on a solid basis: 0.2% by weight) were mixed, and 100 μl of this mixture was added dropwise from one end of the above immunological test strip (receiver), and then developed. The coloring on a capture region after 20 minutes was observed. The results are shown in Table C-3.

EXAMPLE C-4

A Sudan blue-stained particle-labeled avidin-anti-human HBs antibody (labeled component) was obtained in the same manner as in Example C-3. Also, a Sudan blue-stained particle-labeled biotin (conjugate comprising biotin and the second labeling substance) was obtained in the same manner as in Example C-3.

[Preparation of Capture Region]

Anti-human HBs antibodies (rabbit IgG) were diluted with 0.1 M phosphate buffer (pH 7.4), to prepare an aqueous solution having a final concentration of 1 mg/ml. Ten microliters of this aqueous solution was applied to a site of 2 cm from one end of a nitrocellulose membrane filter (Toyo Filter Paper, 5×100 mm), and immediately thereafter the resulting filter was allowed to stand at 37° C. for 1 hour. Thereafter, the nitrocellulose membrane filter was taken out, and immersed into an aqueous solution of 0.1% bovine serum albumin and 0.1% Tween™ 20 for 1 hour.

Subsequently, the nitrocellulose membrane filter was taken out, and allowed to stand at room temperature for 3 hours with air-drying, to give a nitrocellulose membrane filter (immunological test strip) having a capture region in which the anti-human HBs antibodies were immobilized and at one end of the filter a receiver of nonwoven fabric (5×10 mm).

[Preparation of Reagent Region]

Ten microliters of a solution prepared by dissolving a conjugate comprising biotin and the second labeling substance (concentration on a solid basis: 0.02%) in 0.1 M phosphate buffer (pH 7.4) was applied to a 1.5-cm-part between the capture region and receiver of the above immunological test strip, and immediately thereafter, the resulting test strip was allowed to stand at 37° C. for 1 hour, to give an immunological test strip further comprising a reagent region.

[Detection of Human HBs]

One hundred microliters of a mixture of a liquid of a test sample prepared by dissolving human HBs antigens in a physiological saline, and a solution of the labeled components (concentration on a solid basis: 0.2% by weight) was added dropwise to the receiver, and then developed. The coloring on a capture region after 20 minutes was observed. The results are shown in Table C-3.

TABLE C-3

| Concentration of HBs Antigen ng/ml | Evaluation Results Example C-3 | Evaluation Results Example C-4 |
| --- | --- | --- |
| 0 | − | − |
| 0.25 | ± | ± |
| 0.5 | ± | ± |
| 1 | ± | ± |
| 5 | + | + |
| 10 | + | + |
| 100 | + | + |
| 1,000 | + | + |
| 10,000 | + | + |

−: No coloring;
±: slight coloring; and
+: intensive coloring.

From Table C-3, the detection sensitivity for human HBs antigen according to the immunological method of the present invention was about 0.25 ng/ml. Therefore, it is found that the sensitivity of the immunological method of the present invention increases about 40 times compared to the method of Comparative Example C-1.

EXAMPLE C-5

[Preparation of Labeled Component]

One milliliter of an aqueous solution of glutaraldehyde (0.1 mg/ml) was added to 10 ml of a Sudan blue-stained xylenediamine-spacer particle dispersion obtained in the same manner as in Example C-1, and the resulting mixture was allowed to react at room temperature for 2 hours. Thereafter, the resulting reaction mixture was washed by centrifugation with the same buffer as in Example C-1, and adjusted to a dispersion having a concentration of 1% by weight on a solid basis. To 10 ml of the obtained dispersion were added 1 mg of biotin and 1 ml of an anti-human HBs antibody (rabbit IgG, 5 mg/ml), and the resulting mixture was stirred at 10° C. for 24 hours. The resulting mixture was washed by centrifugation with the same buffer as above, and re-dispersed so as to have a concentration of 1% by weight on a solid basis, to give a Sudan blue-stained particle-labeled biotin-anti-human HBs antibody (labeled component), in which the antibodies are bound by covalent bonding.

[Preparation of Conjugate Comprising Avidin and Second Labeling Substance]

One milliliter of an aqueous solution of glutaraldehyde (0.1 mg/ml) was added to 10 ml of a Sudan blue-stained xylenediamine-spacer particle dispersion obtained in the same manner as in Example C-1, and the resulting mixture was allowed to react at room temperature for 2 hours. Thereafter, the resulting reaction mixture was washed by centrifugation with the same buffer as in Example C-1, and adjusted to a dispersion having a concentration of 1% by weight on a solid basis. To 10 ml of this dispersion was added 1 mg of avidin, and the resulting mixture was stirred at 10° C. for 24 hours. The resulting mixture was washed by centrifugation with the same buffer as above, and re-dispersed so as to have a concentration of 1% by weight on a solid basis, to give a Sudan blue-stained particle-labeled avidin (conjugate comprising avidin and the second labeling substance), in which the avidin is bound by covalent bonding.

[Preparation of Capture Region]

In the same manner as in Example C-1, there was obtained a nitrocellulose membrane filter (immunological test strip) having a capture region in which the anti-human HBs antibodies were immobilized and at one end of the filter a receiver of nonwoven fabric (5×10 mm).

[Detection of Human HBs]

A test sample prepared by dissolving human HBs antigens in a physiological saline, the labeled components (concentration on a solid basis: 0.2% by weight), and the conjugate comprising avidin and the second labeling substance (concentration on a solid basis: 0.2% by weight) were mixed. From one end of the above immunological test strip (receiver), 100 µl of this mixture was added dropwise, and then developed. The coloring on a capture region after 20 minutes was observed. The results are shown in Table C-4.

EXAMPLE C-6

A Sudan blue-stained particle-labeled biotin-anti-human HBs antibody (labeled component) was obtained in the same manner as in Example C-5. Also, a Sudan blue-stained particle-labeled avidin (conjugate comprising avidin and the second labeling substance) was obtained in the same manner as in Example C-5.

[Preparation of Capture Region]

Anti-human HBs antibodies (rabbit IgG) were diluted with 0.1 M phosphate buffer (pH 7.4), to prepare an aqueous solution having a final concentration of 1 mg/ml. Ten microliters of this aqueous solution was applied to a site of 2 cm from one end of a nitrocellulose membrane filter (Toyo Filter Paper, 5×100 mm), and immediately thereafter the resulting filter was allowed to stand at 37° C. for 1 hour. Thereafter, the nitrocellulose membrane filter was taken out, and immersed into an aqueous solution of 0.1% bovine serum albumin and 0.1% Tween™ 20 for 1 hour.

Subsequently, the nitrocellulose membrane filter was taken out, and allowed to stand at room temperature for 3 hours with air-drying, to give a nitrocellulose membrane filter (immunological test strip) having a capture region in which the anti-human HBs antibodies were immobilized and at one end of the filter a receiver of nonwoven fabric (5×10 mm).

[Preparation of Reagent Region]

Ten microliters of a solution prepared by dissolving the conjugate comprising avidin and the second labeling substance (concentration on a solid basis: 0.02%) in 0.1 M phosphate buffer (pH 7.4) was applied to a 1.5-cm-part between the capture region and receiver of the above immunological test strip, and immediately thereafter, the resulting test strip was allowed to stand at 37° C. for 1 hour, to give an immunological test strip further comprising a reagent region.

[Detection of Human HBs]

One-hundred microliters of a mixture of a liquid of a test sample prepared by dissolving human HBs antigens in a physiological saline, and a solution of the labeled components (concentration on a solid basis: 0.2% by weight) was added dropwise to the receiver, and then developed. The coloring on a capture region after 20 minutes was observed. The results are shown in Table C-4.

TABLE C-4

| Concentration of HBs Antigen ng/ml | Evaluation Results Example C-5 | Evaluation Results Example C-6 |
|---|---|---|
| 0 | − | − |
| 0.25 | ± | ± |
| 0.5 | ± | ± |
| 1 | ± | ± |
| 5 | + | + |
| 10 | + | + |
| 100 | + | + |
| 1,000 | + | + |
| 10,000 | + | + |

−: No coloring;
±: slight coloring; and
+: intensive coloring.

From Table C-4, the detection sensitivity for human HBs antigen according to the immunological method of the present invention was about 0.25 ng/ml. Therefore, it is found that the sensitivity of the immunological method of the present invention increases about 40 times compared to the method of Comparative Example C-1.

INDUSTRIAL APPLICABILITY

According to the present invention, there is provided a rapid, simple and highly sensitive immunological detection method, and a kit usable for the method.

What is claimed is:

1. An immunological detection method for detecting an analyte which comprises:
   (i) providing a water-absorbent substrate having a capture region thereon, wherein onto said capture region a first immunochemical component of said method which specifically binds to the analyte, is immobilized,
   (ii) forming an immunological complex of analyte, first labeled immunochemical component and second labeled immunochemical component, wherein said first labeled immunochemical component and said second labeled immunochemical component are mixed sequentially or together with said analyte, wherein:
   said first labeled immunochemical component is from a solution comprising (a) said first labeled immunochemical component, which comprises the second immunochemical component of said method, which specifically binds to the analyte and (b) colored latex particles, wherein the colored latex particles are bound to the second immunochemical component; and said second labeled immunochemical component is from a solution comprising (a) said second labeled immunochemical component, which comprises the third immunochemical component of said method, which specifically binds to the second immunochemical component and (b) colored latex particles, wherein the colored latex particles are bound to the third immunochemical component, and (iii) detecting said immunological complex in said capture region.

2. The immunological detection method according to claim 1, wherein the method comprises the following steps:

(1) from one end of a water-absorbent substrate in which a capture region immobilized with said first immunochemical component which specifically binds to an analyte is positioned in a given region on a surface thereof, absorbing a mixture comprising:
a liquid of a test sample comprising said analyte; and
said solution comprising said first labeled immunochemical component, and thereafter developing said first labeled immunochemical component;

(2) thereafter absorbing said solution comprising said second labeled immunochemical component, and thereafter developing said second labeled immunochemical component on the water-absorbent substrate; and
binding the second labeled immunochemical component to the first labeled immunochemical component of the immunological complex captured on the capture region; and (3) thereafter detecting the analyte by assaying color on the capture region.

3. The immunological detection method according to claim 1, wherein the method comprises the following steps:

(1) from one end of a water-absorbent substrate in which a capture region immobilized with said first immunochemical component which specifically binds to an analyte is positioned in a given region on a surface thereof, absorbing a mixture comprising:
a liquid of a test sample comprising said analyte;
said solution comprising said first labeled immunochemical component; and
said solution comprising said second labeled immunochemical component, and thereafter developing said first labeled immunochemical component and said second labeled immunochemical component; and (2) thereafter detecting the analyte by assaying color on the capture region.

4. The immunological detection method according to claim 1, wherein the method comprises the following steps:

(1) absorbing or applying a test sample comprising said analyte on a given region between the capture region and one end of a water-absorbent substrate in which the capture region immobilized with said first immunochemical component which specifically binds to said analyte is positioned in a given region on a surface thereof;

(2) from said one end of a water-absorbent substrate, absorbing said solution comprising said first labeled immunochemical component, and thereafter developing;

(3) thereafter absorbing said solution comprising said second labeled immunochemical component, and binding the second labeled immunochemical component to the first labeled immunochemical component of the immunological complex captured on the capture region; and (4) thereafter detecting the analyte by assaying color on the capture region.

5. The immunological detection method according to claim 1, wherein the method comprises the following steps:

(1) absorbing or applying a test sample comprising said analyte on a given region between said capture region and one end of a water-absorbent substrate in which the capture region immobilized with said first immunochemical component which specifically binds to said analyte is positioned in a given region on a surface thereof;

(2) from said one end of a water-absorbent substrate, absorbing a mixture comprising:
said solution comprising said first labeled immunochemical component; and
said solution comprising said second labeled immunochemical component, and thereafter developing; and (3) thereafter detecting the analyte by assaying color on the capture region.

6. A kit for immunological detection comprising a water-absorbent substrate in which a capture region immobilized with a first immunochemical component which specifically binds to an analyte is positioned in a given region on a surface thereof; a first labeled immunochemical component comprising a second immunochemical component which specifically binds to the analyte, and colored latex particles, wherein the colored latex particles are bound to the second immunochemical component; and a second labeled immunochemical component comprising a third immunochemical component which specifically binds to the second immunochemical component, and colored latex particles, wherein the colored latex particles are bound to the third immunochemical component.

7. The kit according to claim 6, usable for the immunological detection method according to any one of claims 2 to 5.

8. A sandwiched-type immunological detection method wherein at a capture region immobilized with a first immunochemical component which binds to an analyte, the analyte is sandwiched by the first immunochemical component and a labeled component comprising a second immunochemical component which binds to the analyte, a labeling substance and avidin or biotin, wherein the labeling substance is bound to the second immunochemical component, wherein the immunological detection method comprises:

(i) providing a water-absorbent substrate having the capture region and a region where avidin or biotin is maintained;

(ii) from one end of the water-absorbent substrate, absorbing a test sample comprising the analyte; and the labeled component;

(iii) forming together with said first immunochemical component a complex comprising the analyte and the labeled component, the labeled component and the analyte being bound to each other via binding between a biotin and an avidin, and (iv) detecting the analyte by the labeling substance in the complex.

9. The immunological detection method according to claim 8, wherein the labeling substance in the labeled component is bound to the biotin, and wherein the avidin is maintained in a form released by contact with water in a given region between a capture region and one end of a water-absorbent substrate.

10. The immunological detection method according to claim 8, wherein the labeled component is a conjugate comprising the second immunochemical component, a first labeling substance and an avidin, and wherein a conjugate comprising said biotin and a second labeling substance is maintained in a form released by contact with water in a given region between a capture region and one end of a water-absorbent substrate.

11. The immunological detection method according to claim 8, wherein the labeled component is a conjugate comprising the second immunochemical component, a first labeling substance and a biotin, and wherein a conjugate comprising said avidin and a second labeling substance is maintained in a form released by contact with water in a given region between a capture region and one end of a water-absorbent substrate.

12. A kit for immunological detection comprising an immunological test strip comprising a water absorbent substrate having a capture region thereon, the capture region being immobilized with a first immunochemical component which binds to an analyte on the capture region; a labeled component comprising a labeling substance, a biotin and a second immunochemical component which binds to the analyte, wherein the labeling substance is bound to the biotin and the second immunochemical component; and an avidin, wherein the avidin is maintained in a form released by contact with water in a given region between the capture region and one end of the water-absorbent substrate of the immunological test strip.

13. A kit for immunological detection comprising an immunological test strip comprising a water absorbent substrate having a capture region thereon, the capture region being immobilized with a first immunochemical component which binds to an analyte on the capture region; a labeled component comprising a first labeling substance, an avidin and a second immunochemical component binding to the analyte, wherein the first labeling substance is bound to the avidin and the second immunochemical component; and a conjugate comprising a biotin and a second labeling substance, wherein the conjugate comprising a biotin and a second labeling substance is maintained in a form which is released by contact with water in a given region between the capture region and one end of the water-absorbent substrate of the immunological test strip.

14. A kit for immunological detection comprising an immunological test strip comprising a water absorbent substrate and a capture region thereon, the capture region being immobilized with a first immunochemical component which binds to an analyte on the capture region; a labeled component comprising a first labeling substance, a biotin and a second immunochemical component which binds to the analyte, wherein the first labeling substance is bound to a biotin and the second immunochemical component; and a conjugate comprising an avidin and a second labeling substance, wherein the conjugate is maintained in a form which is released by contact with water in a given region between the capture region and one end of the water-absorbent substrate of the immunological test strip.

* * * * *